US010582876B2

(12) United States Patent
Suzuki et al.

(10) Patent No.: US 10,582,876 B2
(45) Date of Patent: Mar. 10, 2020

(54) GLASSES-LENS ASSESSMENT METHOD, GLASSES-LENS DESIGN METHOD USING ASSESSMENT METHOD, AND CALCULATION METHOD FOR VISUAL-PERFORMANCE CHARACTERISTICS OF TEST SUBJECT WHEN VIEWING OBJECT THROUGH LENS

(71) Applicants: Tokai Optical Co., Ltd., Okazaki-shi, Aichi (JP); Inter-University Research Institute Corporation National Institutes of Natural Sciences, Okazaki-shi, Aichi (JP)

(72) Inventors: Masaya Suzuki, Okazaki (JP); Naoya Kumagai, Okazaki (JP); Koji Inui, Okazaki (JP); Yasuyuki Takeshima, Okazaki (JP); Ryusuke Kakigi, Okazaki (JP)

(73) Assignees: Tokai Optical Co., Ltd., Aichi (JP); Inter-University Research Institute Corporation National Institutes of Natural Sciences, Aichi (JP)

( * ) Notice: Subject to any disclaimer, the term of this patent is extended or adjusted under 35 U.S.C. 154(b) by 757 days.

(21) Appl. No.: 15/027,860

(22) PCT Filed: Oct. 6, 2014

(86) PCT No.: PCT/JP2014/076663
§ 371 (c)(1),
(2) Date: Apr. 7, 2016

(87) PCT Pub. No.: WO2015/053210
PCT Pub. Date: Apr. 16, 2015

(65) Prior Publication Data
US 2016/0242670 A1    Aug. 25, 2016

(30) Foreign Application Priority Data

Oct. 8, 2013 (JP) ................................ 2013-210872

(51) Int. Cl.
*G02C 7/02* (2006.01)
*A61B 5/0484* (2006.01)
(Continued)

(52) U.S. Cl.
CPC ........ *A61B 5/04842* (2013.01); *A61B 3/0025* (2013.01); *A61B 3/036* (2013.01);
(Continued)

(58) Field of Classification Search
CPC ....... A61B 3/036; A61B 3/10; A61B 5/04842; A61B 5/04012; G02C 7/024; G02C 7/27
See application file for complete search history.

(56) References Cited

U.S. PATENT DOCUMENTS 4,697,598 A * 10/1987 Bernard ................ A61B 3/103
351/205

FOREIGN PATENT DOCUMENTS

JP    H11-125799      5/1999
JP    2011-197556    10/2011
(Continued)

OTHER PUBLICATIONS

International Search Report for PCT/JP2014/076663 dated Jan. 20, 2015 (6 pages).

*Primary Examiner* — Puya Agahi
(74) *Attorney, Agent, or Firm* — Bookoff McAndrews, PLLC

(57) ABSTRACT

The invention provides an evaluation method capable of objectively evaluating average visual perception for a comparatively long period of time when a subject looks through an eyeglass lens to be evaluated, time-dependent change in
(Continued)

visual perception, and visual perception when looking with both eyes, and the invention provides a design method, and the invention provides a calculation method for calculating characteristics of visual perception of the subject when viewing an object through a lens.

[Solution] A subject is allowed to wear a lens to be evaluated, the subject is allowed to induce brain activity by allowing the subject to view a changing visual stimulus object that induces periodic brain activity through the lens to be evaluated, a change in faint electric current caused by the brain activity is time-dependently recorded as a change in a magnetic field (magnetic flux density) by use of a magnetoencephalograph, one or more among an amplitude, a power value, and a phase in a frequency that is an inverse number of a period of the periodic brain activity is or are calculated through fast Fourier analysis of the waveform, and the lens to be evaluated and the characteristic of visual perception of the subject are evaluated based on a magnitude of an amplitude or of a power value obtained above or based on a slowness/fastness of a phase obtained above.

25 Claims, 18 Drawing Sheets

(51) Int. Cl.
*A61B 5/00* (2006.01)
*A61B 5/04* (2006.01)
*A61B 3/00* (2006.01)
*A61B 3/036* (2006.01)
*A61B 3/08* (2006.01)
*G02C 7/06* (2006.01)
*A61B 3/10* (2006.01)

(52) U.S. Cl.
CPC ............ *A61B 3/08* (2013.01); *A61B 5/04009* (2013.01); *A61B 5/04012* (2013.01); *A61B 5/4005* (2013.01); *A61B 5/7257* (2013.01); *G02C 7/027* (2013.01); *G02C 7/028* (2013.01); *A61B 3/10* (2013.01); *A61B 5/04008* (2013.01); *A61B 2562/0223* (2013.01); *G02C 7/024* (2013.01); *G02C 7/061* (2013.01)

(56) References Cited

FOREIGN PATENT DOCUMENTS

| | | | | |
|---|---|---|---|---|
| JP | 2012-152568 | 8/2012 | | |
| JP | 2013-011877 | 1/2013 | | |
| JP | 2013011877 A | * | 1/2013 | ............... A61B 3/10 |
| WO | WO 2010/035726 A1 | 4/2010 | | |
| WO | WO-2010035726 A1 | * | 4/2010 | ............. G02C 7/027 |

* cited by examiner (a)

(b)

(a)

(b)

(a)

(b)

(a)

(b)

(c)

Right and left eye differ from each other in the position on the lens through which the sight line passes, and therefore it is important to evaluate visual perception through the lens at the secondary position of eye and the tertiary position of eye.

(a)  (b)

(a)  (b)

GLASSES-LENS ASSESSMENT METHOD, GLASSES-LENS DESIGN METHOD USING ASSESSMENT METHOD, AND CALCULATION METHOD FOR VISUAL-PERFORMANCE CHARACTERISTICS OF TEST SUBJECT WHEN VIEWING OBJECT THROUGH LENS

This application is a U.S. national stage filing under 35 U.S.C. § 371 of International Application No. PCT/JP2014/076663, filed on Oct. 6, 2014, incorporated by reference herein in its entirety, which claims the benefit of priority to Japanese Patent Application No. 2013210872, filed on Oct. 8, 2013.

TECHNICAL FIELD

The present invention relates to an evaluation method for evaluating an eyeglass lens by use of the evoked activity in a steady state of the brain, a design method for designing an eyeglass lens by use of the evaluation method, and a calculation method for calculating characteristics of subject's visual perception when viewing an object through the lens.

BACKGROUND ART

In a performance evaluation of experimental design when an eyeglass lens is designed and developed or in a product comparison when a user considers the purchase of eyeglass lenses, there is a desire to employ a technique for evaluating objectively how well a view through lens design is visually perceived in practice. A human being views an object with two eyes, and therefore there is another desire to objectively evaluate visual perception when viewing an object with both eyes. There is still another desire to provide eyeglass lenses suitable for a user by calculating visual characteristics of the user or by calculating how to use the sight line of the user when the user purchases eyeglass lenses in the form of objective numerical values. The reason is that it is easy to choose eyeglasses suitable for a user if visual characteristics of the user and how to use the sight line of the user are beforehand known.

An visual acuity test that uses, for example, Landolt rings, E marks, or hiraganas, which is an existing method for ascertaining user's visual perception, is performed, and, as a result, it is possible to ascertain how well a user visually perceives such objects through a lens in accordance with user's subjectivity. Additionally, the use of, for example, an autorefractometer makes it possible to objectively measure the refractive power of user's eyes.

CITATION LIST

Patent Documents

Patent Document 1: Japanese Published Unexamined Patent Application No. 2012-152568
Patent Document 2: Japanese Published Unexamined Patent Application No. 2013-11877
Patent Document 3: Japanese Published Unexamined Patent Application No. H11-125799

DISCLOSURE OF INVENTION

Technical Problem

However, in the aforementioned existing eyesight ascertaining method, the eyesight is often ascertained as momentary maximum eyesight during measurement performed in a short period of time, and, when eyesight is ascertained by use of, for example, Landolt rings, the eyesight is sometimes regarded as being exercised if a Landolt ring is discriminated even momentarily. The same applies to a case in which the refractive power of an eye is objectively measured by an autorefractometer, and is sometimes measured while the eyesight changes only momentarily during measurement depending on the state of a tear fluid on the surface of the eye.

Additionally, eyesight is known to be lowered by reading and driving, by continuous use of eyes in personal computer operations or the like, by dryness of an eye surface, or by muscle fatigue resulting from adjustments, and visual perception is changed by blinking or the like. Therefore, it is important to evaluate how well an object is visually perceived for a somewhat long period of time or to evaluate how visual perception changes with the lapse of time, not to evaluate momentary visual perception during measurement.

Patent Document 1 is first mentioned as an example of a means for solving these problems.

Patent Document 1 proposes to measure functional visual acuity by displaying index marks (e.g., Landolt rings), by receiving a subject's response by means of an input device, by determining whether the response is correct or not, and by repeatedly presenting index marks that differ in size from each other. The technique proposed by this document is meaningful in the fact that it is possible to measure a time-dependent change in eyesight and in the fact that it is possible to calculate a time-dependent change in visual perception or calculate average visual perception in a time unit, not calculate momentary visual perception, by integrating the time-dependent change of eyesight values acquired by measurement. However, the evaluation method of Patent Document 1 depends on a subjective determination of whether indexes, such as Landolt rings, have been discriminated, and therefore it is difficult to objectively evaluate the true state of the visual perception of the subject.

Patent Document 2 that is a preceding invention made by the inventors is mentioned as a method for objectively evaluating visual perception through an eyeglass lens. Patent Document 2 discloses that, when a subject views a visual stimulus object through a to-be-evaluated lens, the evoked activity of the brain's visual cortex or the like is measured by an electroencephalograph or a magnetoencephalograph, and the eyeglass lens is evaluated based on the magnitude (amplitude) of its activity or based on a period of time (latency) from the reception of a visual stimulus to the occurrence of a change in its activity. This eyeglass-lens evaluation technique disclosed by Patent Document 2 is meaningful in the fact that it becomes possible to objectively evaluate extremely-delicate visual perception through the lens by using not the voluntary brain activity but the evoked brain activity. However, a visual evoked potential or a visual evoked magnetic field is used for the evoked brain activity such that brain waves or brain magnetic fields that occur after the presentation of a visual stimulus are averaged, and therefore, disadvantageously, the subject is required to control a blink in accordance with the presentation of a stimulus image (i.e., the subject is required to be skilled), and a measurement period of time becomes long because an averaging operation must be normally performed fifty times or more, and an upper part of the lens is required to be inventively evaluated because a lower visual field reacts much more than an upper visual field in most cases.

Additionally, as shown in Patent Document 3, there is a desire to make easy-to-use lenses for both eyes in consideration of the aberration distribution of a progressive power lens when an object is viewed with both eyes. However, disadvantageously, visual perception cannot be objectively evaluated when an object is actually viewed with both eyes through progressive lenses although there have so far been some proposals to simulate the visual perception of both eyes in accordance with an optical design technique.

The present invention has been made in consideration of these problems of the conventional techniques. An object of the present invention is to provide an evaluation method that is capable of objectively evaluating average visual perception obtained during a comparatively long period of time when a subject views an object through an eyeglass lens that is to be evaluated, capable of objectively evaluating a time-dependent change in visual perception, and capable of objectively evaluating visual perception when a subject views an object with both eyes, and is to provide a design method that uses the evaluation method, and is to provide a calculation method for calculating characteristics of subject's visual perception when an object is viewed through a lens.

Solution to Problem

To solve the aforementioned problems, the gist of a first means resides in that the evaluation method includes allowing a subject to wear a lens to be evaluated, allowing the subject to induce brain activity by allowing the subject to view a changing visual stimulus object that induces periodic brain activity through the lens to be evaluated, obtaining the brain activity as a waveform of an electrical signal, calculating one or more among an amplitude, a power value, and a phase in a frequency that is an inverse number of a period of the periodic brain activity through analysis of the waveform, and evaluating the lens to be evaluated based on a magnitude of an amplitude or of a power value obtained above or based on a slowness/fastness of a phase obtained above.

The gist of a second means resides in that, in addition to the arrangement of the first means, a point (hereinafter, referred to as a "fixation point") at which the subject is allowed to gaze is presented to the subject when the subject is allowed to view the visual stimulus object through the lens to be evaluated.

The gist of a third means resides in that, in addition to the second means, the fixation point is displayed so as to be movable, and the subject is allowed to view the fixation point while the subject is moving a sight line.

The gist of a fourth means resides in that, in addition to the second means or the third means, the visual stimulus object is set to be movable.

The gist of a fifth means resides in that, in addition to any one of the first to fourth means, the visual stimulus object is viewed by both eyes.

The gist of a sixth means resides in that, in addition to the fifth means, one or more among an amplitude, a power value, and a phase that have been obtained as a result of viewing the visual stimulus object by both eyes and that have been analyzed is or are evaluated by comparison with one or more among an amplitude, a power value, and a phase that have been obtained as a result of viewing the visual stimulus object by one eye and that have been analyzed.

The gist of a seventh means resides in that, in addition to the fifth means, one or more among an amplitude, a power value, and a phase that have been obtained as a result of viewing the visual stimulus object by both eyes and that have been analyzed is or are evaluated by comparison with one or more among an amplitude, a power value, and a phase that have been obtained as a result of viewing the visual stimulus object by left and right eyes through lenses having mutually different conditions and that have been analyzed.

The gist of an eighth means resides in that, in addition to any one of the fifth to seventh means, balance of visual perception between both eyes is evaluated by one or more among an amplitude, a power value, and a phase that have been obtained as a result of viewing the visual stimulus object by both eyes and that have been analyzed.

The gist of a ninth means resides in that, in addition to any one of the first to eighth means, one or more among an amplitude, a power value, and a phase that have been obtained as a result of viewing the visual stimulus object by a dominant eye and that have been analyzed is or are evaluated by comparison with one or more among an amplitude, a power value, and a phase that have been obtained as a result of viewing the visual stimulus object by a non-dominant eye and that have been analyzed.

The gist of a tenth means resides in that, in addition to any one of the first to ninth means, in the analysis of the waveform, a time unit for use in analysis smaller than a total measurement time (hereinafter, this time unit is referred to as an "analysis window") is set, and the analysis is performed by the unit of the analysis window.

The gist of an eleventh means resides in that, in addition to any one of the first to tenth means, a plurality of lenses to be evaluated each of which is defined in the preceding means and that have mutually different lens characteristics are prepared.

The gist of a twelfth means resides in that, in addition to any one of the first to eleventh means, the visual stimulus object is composed of one line segment or of a plurality of line segments, and visual perception that changes depending on an axial direction of astigmatism is evaluated.

The gist of a thirteenth means resides in that, in addition to any one of the first to eleventh means, the visual stimulus object is composed of one circle or of a plurality of circles, and a size of an astigmatic component is evaluated without evaluating visual perception that changes depending on an axial direction of astigmatism.

The gist of a fourteenth means resides in that, in addition to the twelfth means, the visual perception that changes depending on the axial direction of astigmatism is evaluated by alternately showing a first figure and a second figure that are components of the visual stimulus object, in which the first figure is composed of one line segment or of a plurality of line segments by which directionality with respect to a direction is perceivable, and the second figure is composed of one line segment or of a plurality of line segments by which directionality with respect to a direction is perceivable and by which directionality in a direction differing from the directionality of the first figure is perceivable.

The gist of a fifteenth means resides in that, in addition to the thirteenth means, a size of an astigmatic component is evaluated without evaluating visual perception that changes depending on an axial direction of astigmatism by alternately showing a first figure and a second figure that are components of the visual stimulus object, in which the first figure is composed of one circle or of a plurality of circles by which directionality is unperceivable, and the second figure is composed of one circle or of a plurality of circles by which directionality different in arrangement from the directionality of the first figure is unperceivable.

The gist of a sixteenth means resides in that, in addition to any one of the first to fifteenth means, the visual stimulus object is presented at a secondary position of eye of the subject or at a tertiary position of eye of the subject.

The gist of a seventeenth means resides in that, in addition to any one of the first to sixteenth means, the visual stimulus object is continuously displayed without providing a period of time during which the visual stimulus object is not displayed.

The gist of an eighteenth means resides in that, in addition to any one of the first to sixteenth means, the visual stimulus object is discontinuously displayed by providing a period of time during which the visual stimulus object is not displayed.

The gist of a nineteenth means resides in that, in addition to any one of the first to eighteenth means, the visual stimulus object is composed of a plurality of and two or more kinds of visual stimulus objects, and the plurality of visual stimulus objects are equal in brightness to each other.

The gist of a twentieth means resides in that, in addition to any one of the first to nineteenth means, the frequency that is an inverse number of a period of the periodic brain activity is 4 to 60 Hz.

The gist of a twenty-first means resides in that, in addition to the twentieth means, the frequency that is an inverse number of a period of the periodic brain activity is 4 to 7 Hz or 14 to 19 Hz.

The gist of a twenty-second means resides in that, in addition to any one of the first to twenty-first means, the lens to be evaluated is a progressive power lens.

The gist of a twenty-third means resides in that, in addition to any one of the first to twenty-second means, the brain activity is a visual evoked magnetic field in a steady state.

The gist of a twenty-fourth means resides in that, in addition to any one of the first to twenty-second means, the brain activity is a visual evoked potential in a steady state.

The gist of a twenty-fifth means resides in that eyeglass lenses are designed based on an evaluation result calculated according to the evaluation method of any one of the first to twenty-fifth means.

The gist of a twenty-sixth means resides in that, in addition to the twenty-fifth means, the design method includes a first step of, as a result of analyzing two or more kinds of lenses to be evaluated, obtaining a difference in an optical performance value between a most highly evaluated lens among the lenses to be evaluated and another lens among the lenses to be evaluated, a second step of giving a part of the difference obtained in the first step as a correction value of the optical performance value of the most highly evaluated lens thereamong and calculating a new lens shape with a corrected optical performance value as a design target value so as to set a reference lens to be evaluated, a third step of, in the following items (A) and (B), obtaining a difference in an optical performance value between a most highly evaluated lens among the lenses to be evaluated and another lens among the lenses to be evaluated, (A) the reference lens to be evaluated and the most highly evaluated lens there among, (B) the reference lens to be evaluated, the most highly evaluated lens there among, and one or a plurality of lenses to be evaluated that has or have been newly added, and a fourth step of giving a part of the difference obtained in the third step as a correction value of the optical performance value of the most highly evaluated lens there among and calculating a new lens shape with a corrected optical performance value as a design target value so as to set the reference lens to be evaluated, in which an eyeglass lens suitable for the subject is designed by reducing the difference while repeatedly performing the third step and the fourth step.

The gist of a twenty-seventh means resides in that the calculation method includes allowing the subject to wear a predetermined lens, allowing the subject to induce brain activity by allowing the subject to view a changing visual stimulus object that induces periodic brain activity through the lens, obtaining the brain activity as a waveform of an electrical signal, calculating one or more among an amplitude, a power value, and a phase in a frequency that is an inverse number of a period of the periodic brain activity through analysis of the waveform, and calculating a characteristic of visual perception of the subject in viewing an object through the lens based on a magnitude of an amplitude or of a power value obtained above or based on a slowness/fastness of a phase obtained above.

The gist of a twenty-eighth means resides in that, in addition to the twenty-seventh means, a lens is designed based on a characteristic of visual perception of the subject measured in the twenty-seventh means.

In the aforementioned arrangement, a subject is first allowed to wear a lens to be evaluated, and the subject is allowed to induce brain activity by allowing the subject to view a changing visual stimulus object that induces periodic brain activity through the lens to be evaluated, and the brain activity when the subject views the changing visual stimulus object that induces periodic brain activity is obtained as a waveform of an electrical signal. Although the waveform of the electrical signal includes information on many wavelength regions, one or more among an amplitude, a power value, and a phase in a frequency that is an inverse number of a period of the periodic brain activity is or are calculated through analysis. In other words, for example, if periodic brain activity is performed with a period of 250 ms (milliseconds), the frequency of this change for each unit (one second here) is 1/0.25=4 Hz, and therefore, in this case, one or more among the amplitude, the power value, and the phase is or are calculated concerning a frequency of 4 Hz as a result of analysis. Although what is required is 4 Hz, an amplitude, a power value, and a phase in other frequencies may be calculated together therewith. The lens is evaluated based on the magnitude of the amplitude or of the power value or based on the slowness/fastness of the phase obtained in this way. At this time, the lens condition becomes more desirable in proportion to an increase in the strength of the calculated amplitude or power value. The reason is that, when the subject is allowed to view a changing visual stimulus object that induces periodic brain activity as a visual stimulus, the periodicity given as a stimulus is efficiently transmitted to the brain's visual cortex as a piece of information in a lens having a desirable condition. Additionally, the lens condition becomes more desirable in proportion to an increase in the slowness/fastness of the calculated phase in comparison with a to-be-compared lens. The reason is that, when the subject is allowed to view a changing visual stimulus object that induces periodic brain activity as a visual stimulus, the periodicity given as a stimulus is fast transmitted to the brain's visual cortex as a piece of information in a lens having a desirable condition. In the embodiments described later, for example, a lens is also free to be evaluated by a means other than the magnitude of an amplitude, i.e., to be evaluated by the magnitude of a power value or by the slowness/fastness of a phase. Additionally, preferably, an evaluation is made by a combination of two or more evaluation results, such as a combination of an amplitude and a phase or a combination of a power value and a phase, without being limited to a case in which the amplitude, the power value, and the phase are individually used for an evaluation, because the influence of a measurement noise can be decreased.

Here, the term "power value" denotes the magnitude of energy of a component of a frequency, and the dimension is the square of an amplitude. Although the power value deals with a numerical value that is roughly the square of an amplitude in most cases, it may be treated by being converted into, for example, the value per unit time or the value per normalized frequency.

The slowness/fastness of a phase is capable of being recognized, for example, as a difference (gap) between two or more phases or as a difference (gap) with, for example, an average value of past phases that have already been obtained in the form of data.

Additionally, an evaluation value based on the magnitude of an amplitude or of a power value or based on the slowness/fastness of a phase is capable of being calculated by simultaneously recording and comparing a plurality of brain regions with each other even in single measurement. Therefore, it is preferable to simultaneously measure a plurality of brain regions. For example, in the primary visual cortex and the tertiary visual cortex, generally, the tertiary visual cortex shows larger brain activity with respect to complicated visual information, and therefore it is preferable to obtain an evaluation value by a comparison between amplitudes or power values of the primary and tertiary visual cortexes when a complicated image is viewed as a visual stimulus object. Additionally, for example, in the primary visual cortex and the sixth visual cortex, generally, visual information is transmitted faster in the primary visual cortex than in the sixth visual cortex, and therefore it is preferable to obtain an evaluation value by a comparison between phases of the primary and sixth visual cortexes. A combination of brain regions used for an evaluation is one example, and the present invention is not limited to this. Here, preferably, in order to induce periodic brain activity, the subject is allowed to view a visual stimulus object that induces subject's brain activity at the frequency of four times or more per second (i.e., a period of 250 milliseconds or less). When a visual stimulus is presented, the activity of neurons in the brain's visual cortex is completed within roughly 300 milliseconds or less, and therefore, if the visual stimulus is presented four times or more per second, the neuron activity of a next visual stimulus is induced before the neuron activity of a previous visual stimulus is completed, and therefore the reason is that it is possible to induce not neuron activity by a single visual stimulus but periodic brain activity. Here, preferably, the frequency (period) of a change of a visual stimulus object viewed by a subject is set from the frequency (period) of periodic brain activity intended to be analyzed. This makes it possible to create the period of neuron activity of a brain region of a targeted brain's visual cortex. Additionally, the frequency (period) of a change of a visual stimulus object viewed by the subject may be frequencies that have a multiple relationship with the period of neuron activity without being limited to synchronization with the period of targeted neuron activity. In that case, the same effect is likewise fulfilled.

For example, in a case in which the brain activity of 20 Hz (i.e., a period of 50 milliseconds) is intended to be induced as periodic brain activity, and its brain activity is intended to be analyzed, a subject is allowed to view a visual stimulus object, by which the neuron activities of the brain region of a targeted brain's visual cortex become substantially the same, at a period of 50 milliseconds so that neuron activity occurs in the brain's visual cortex at a period of 50 milliseconds.

Here, the term "analysis" in the present invention denotes decomposing the waveform of an electrical signal for each frequency and obtaining the waveform of a frequency component that is an inverse number of a variable period. In an analysis technique, it is possible to calculate an amplitude, a power value, and a phase by decomposing a waveform obtained by use of, for example, Fourier analysis including discrete Fourier analysis, wavelet analysis, or Hilbert transform for each frequency.

The term "changing visual stimulus object" generally denotes an image that singly or complexly includes a change in figure shape or a change in color, in brightness, and in contrast, and herein this term is a concept that also includes a mere light spot not having a shape such as a figure. Even if the same image is used, it is possible to create such a change by repeatedly performing "to show" and "not to show." Additionally, instead of "to show" and "not to show," it is also possible to realize such a change by alternately changing brightness, color, and shape while continuing to show. Possible examples of images include line segments formed of simple figures, such as latticed patterns or checkered patterns, a combination of painted-out squares, and a plurality of circles (which may be or may not be painted out). Additionally, it is also possible to use a complicated image, such as a photograph showing scenery or persons, not a simple image such as lattice, line, or circle. For example, it is known that eyes can be brought into a relaxed state if distant scenery is shown, and a distinctive brain reaction can be measured in, for example, a fusiform gyms if a person's face is shown, and therefore the complicated image is useful as a visual stimulus object.

It is possible to apply the change of the visual stimulus object to a more specific evaluation of an astigmatic component of a lens. The astigmatic component of a lens denotes, for example, astigmatism that occurs at a lens peripheral part of a spherical lens and that occurs at a lateral part of a progressive power lens without being limited to astigmatism (C diopter power) in the prescription diopter power of a lens. This astigmatic component, i.e., this astigmatism occurs from a difference in the image formation state on the retina between a greatest meridian having the strongest refractive power and a least meridian having the weakest refractive power, and the difference in diopter power between the greatest meridian and the least meridian is the astigmatic difference, and the half of the difference in diopter power between the greatest meridian and the least meridian is astigmatism. The astigmatic component or the astigmatism has directionality, and what shows its directionality is the axis of astigmatic vision and the axis of astigmatism.

It is possible to evaluate visual perception that changes depending on the axial direction of astigmatism, for example, by forming a visual stimulus object (image) of one or more line segments that enables perceiving directionality with respect to a direction. This uses a change in strength of the neuron activity of the brain's early visual cortex caused by a difference in visual perception because a line segment having an easily-viewed direction depending on the axial direction of astigmatism, i.e., a line segment formed on the retina as a clear image and a line segment having a difficulty-viewed direction depending on the axial direction of astigmatism, i.e., a line segment formed on the retina as a defocused image are obtained by using a line segment that enables perceiving directionality as a visual stimulus object.

Additionally, it is possible to evaluate the magnitude of an astigmatic component, for example, by forming a visual stimulus object (image) of one or more circles without evaluating visual perception that changes depending on the axial direction of astigmatism. If the visual stimulus object is a line segment, the line segment has directionality, and therefore an image formation state on the retina changes depending on the axial direction of astigmatism whereas, if the visual stimulus object is a circle, the circle has no directionality, and therefore if there is equality in the amount of astigmatism and there is a difference in the axial direction, substantially the same image formation state is reached although a slight influence, such as Listing's law, is caused when the image formation state on the retina is rotated, and therefore the strength of the neuron activity of the brain's early visual cortex does not depend on the axial direction of astigmatism, and is influenced by the amount of astigmatism and by other aberrations (e.g., diopter power error). Therefore, it is possible to evaluate the magnitude of an astigmatic component by forming a visual stimulus object of one or more circles without evaluating visual perception that changes depending on the axial direction of astigmatism.

Additionally, in the thus performed evaluation, it is preferable to make an evaluation by alternately displaying a first figure and a second figure different from the first figure that is equal in the brightness of the entire visual stimulus object, because the influence of brightness can be removed from a brain reaction.

The process of obtaining brain activity as a waveform of an electrical signal specifically denotes the process of time-dependently recording a change in slight electric current caused by brain activity with a brain wave as a change in electric potential (voltage) by use of an electroencephalograph or denotes the process of time-dependently recording a brain magnetic field as a change in the magnetic field (in the magnetic flux density) by use of a magnetoencephalograph.

Here, a changing visual stimulus object that induces periodic brain activity must be output at an accurate temporal timing, and the period of periodic brain activity must has such a duration as to be perceivable by the brain of a subject. If the period is too short, a changing state is not transmitted to the subject's brain, thus making it impossible to obtain periodic evoked brain activity aimed here. Therefore, the frequency is preferably 4 to 60 Hz, and more preferably 4 to 7 Hz or 14 to 19 Hz. The range of 8 to 13 Hz is a range (so-called a wave range) in which a reaction in voluntary brain activity occurs, and it becomes difficult to draw a distinction between this voluntary brain activity and the evoked periodic brain activity, and hence there is a case in which, in 20 Hz and 30 Hz, brain activities other than the evoked periodic brain activity are measured, and therefore 4 to 7 Hz or 14 to 19 Hz is employed in order to avoid that case. In 4 to 7 Hz and 14 to 19 Hz, it is preferable to use the range of 14 to 19 Hz that is a frequency domain in which a voluntary brain wave occurs smaller in quantity than the range of 4 to 7 Hz. Additionally, when a visual stimulus object is presented at the frequency of 30 to 60 Hz, the switching (flickering) between images that are visual stimulus objects does not worry a subject or allows the subject to be perceivable only by a brain reaction without allowing the subject to visually perceive it, and therefore that is desirable when tiredness caused by the visual stimulus object is intended to be reduced or when deviation in the sight line is intended to be reduced.

Concerning lenses to be evaluated, periodic brain activity measured with respect to a single to-be-evaluated lens may be evaluated, or periodic brain activity measured with respect to a plurality of prepared to-be-evaluated lenses that are mutually different in the lens characteristic may be evaluated. The evaluation does not necessarily lead to the selection of a lens having the best result. Here, strictly speaking, the point resides in the fact that the evaluation makes it possible to obtain objective information on visual perception through a lens.

Additionally, it is recommended to present a fixation point when the subject is allowed to view a visual stimulus object through a to-be-evaluated lens. Preferably, a changing visual stimulus object that induces periodic brain activity is included to a peripheral visual field of a viewing angle of eight degrees or more not to a central visual field (a viewing angle of four degrees or less) within a subject's visual field, and, in that case, a comparatively large range is occupied, and therefore it is recommended to set a fixation point in order to consolidate where the subject is viewing within the visual stimulus object. If a fixation point is not provided, the sight line will unconsciously move simultaneously with the switching between visual stimulus objects, and it will become difficult to measure a targeted brain reaction, and the movement of the sight line will cause a noise during measurement. Particularly, in order to perform measurement while reducing a noise, it is preferable to display the fixation point in front of a changing visual stimulus object that induces periodic brain activity, and it is preferable to instruct the subject to view not the changing visual stimulus object that induces periodic brain activity on the background but the fixation point. However, in a case in which the subject is a small child or in which the sight line is not easily fixed, measurement might be performed with a lesser noise when the fixation point is not displayed, and therefore it is important to appropriately adjust the display of the fixation point while depending on the subject.

Additionally, it is recommended to employ a presentation method in which a visual stimulus object is movably displayed, and the subject is allowed to view the moving visual stimulus object while moving the sight line of the subject. The reason is that visual perception through a to-be-evaluated lens when the sight line is moved is objectively evaluated. At this time, it is preferable to move the fixation point displayed at the front together with the visual stimulus object. The visual stimulus object that induces periodic brain activity and that serves as a background is moved together with the fixation point, and the subject is allowed to chase it with the sight line, and, as a result, if visual perception through the lens is the same, the image formation state on the retina will become substantially constant without depending on the direction of the sight line. Therefore, it becomes possible to evaluate visual perception at a position on the lens through which the sight line has passed by moving the visual stimulus object that serves as a background together. Additionally, it is preferable to allow the subject to view the visual stimulus object with both eyes, because it becomes the same condition as in actual viewing. When looking a lateral side while viewing the object with both eyes as in FIG. 15, coordinates in which the sight line passes through the lens differ between the right and left eyes, and therefore a difference in visual perception arises between the right and left eyes, and therefore it is important to objectively measure visual perception with both eyes. Additionally, it is preferable to evaluate one or more among an amplitude, a power value, and a phase that have been obtained as a result of viewing the visual stimulus object by both eyes and that have been analyzed by comparison with one or more among an amplitude, a power value, and a phase that have been obtained as a result of viewing the visual stimulus object by one eye and that have been analyzed, because a difference in visual perception between viewing with both eyes and viewing with one eye is evaluated, or a difference in visual perception between the dominant eye and the non-dominant eye is evaluated. It is preferable to allow the dominant eye and the non-dominant eye to alternately wear lenses having mutually different conditions at this time for comparison, because it is possible to evaluate a difference in visual perception between the dominant eye and the non-dominant eye. Additionally, it is possible to evaluate the balance of visual perception of both eyes by one or more among an amplitude, a power value, and a phase that have been obtained as a result of viewing the visual stimulus object by both eyes and that have been analyzed. Although unclear visual perception is often given when it is viewed by both eyes even if excellent visual perception is obtained when it is viewed by each single eye, the use of the present invention makes it possible to make an evaluation to adjust the balance of visual perception of both eyes in such a case. In other words, it is possible to make an evaluation about whether both eyes are in a truly excellent visually-perceivable state.

Here, the term "dominant eye" is a characteristic known as part provided with a human being in the same way as a "dominant hand," and is one of both eyes that is much used unconsciously when looking by both eyes. The dominant eye can be determined, for example, by judging which one of both eyes is used to view a point while indicating the point about several meters distant. In many cases, the dominant eye is the same as a predominant eye treated preferentially between right and left eyes, and yet there are cases in which the dominant eye sometimes differs from the predominant eye. In such cases, for example, it is preferable to allow the predominant eye and the non-predominant eye to alternately wear mutually different lenses, respectively, for comparison instead of the dominant and non-dominant eyes.

Additionally, it is preferable to present a visual stimulus object at a secondary position of eye or a tertiary position of eye of the subject. The primary position of eye denotes a state in which the subject views the front, and the secondary position of eye denotes a case in which the subject views any one of the upper, lower, right, and left axes, and the tertiary position of eye denotes a case in which the subject views a diagonal direction. In lenses, naturally, the front is well viewed, and the reason is that it becomes important to rather allow the subject to firmly view such a range in a lens in which additional diopter power is provided as in a progressive power lens. In a single vision lens, the reason is that visual perception not at a lens center (primary position of eye) but at a lens peripheral part becomes important, and therefore that is objectively evaluated.

Additionally, when the subject is allowed to view a visual stimulus object, it is preferable to continuously display the visual stimulus object without providing a period of time during which the visual stimulus object is not displayed. The reason is that a brain reaction caused by the display and the non-display of the stimulus is removed from measurement results by continuing displaying the stimulus, and a stable measurement result is obtained. In that case, it is possible to also remove a brain reaction caused by a change in brightness from measurement results and measure only a brain reaction concerning visual perception particularly by displaying visual stimulus objects that are the same in brightness.

Additionally, it is preferable to discontinuously display a visual stimulus object by providing a period of time during which the visual stimulus object is not displayed. The reason is that it becomes possible to measure a stronger brain reaction because a change in brightness is applied to the visual stimulus object when the visual stimulus object is displayed and is not displayed.

Additionally, in waveform analysis, it is preferable to set an analysis window for use in analysis smaller than the total measurement time and perform analysis with this analysis window unit. It is possible to objectively perform numeric conversion of average visual perception during a somewhat long time by widely setting the analysis window. On the other hand, it is possible to objectively measure a time-dependent change in visual perception from a brain reaction by narrowly setting the analysis window and by performing analysis with a plurality of windows with respect to a measurement result. At this time, it becomes possible to evaluate a time-dependent change in visual perception in more detail by performing analysis while continuously moving the analysis window.

Additionally, in the aforementioned arrangement, the subject is allowed to wear a predetermined lens, and the subject is allowed to induce brain activity by allowing the subject to view a changing visual stimulus object that induces periodic brain activity, and the brain activity when the subject views a changing visual stimulus object that induces periodic brain activity is obtained as a waveform of an electrical signal, and one or more among an amplitude, a power value, and a phase in a frequency that is an inverse number of a period of the periodic brain activity is or are calculated through analysis. Thereafter, a characteristic of visual perception of the subject in viewing an object through the lens is calculated based on the magnitude of an amplitude or of a power value thus obtained or based on the slowness/fastness of a phase thus obtained. In other words, the essentials of the present invention are to allow the subject to view a visual stimulus object through a lens and to induce periodic brain activity. As a result, one is to evaluate the lens itself and hence select a better lens for the subject, and another one is to analyze a characteristic about how the subject visually perceives the object through the lens and to select a better lens for the subject in accordance with the tendency of the visual perception of each individual subject.

Additionally, it is preferable to design an eyeglass lens by use of the eyeglass-lens evaluation method. The eyeglass-lens design is to determine lens design information by controlling refractive power and the like in each lens point resulting from the control of the lens shape and the like of the eyeglass lens when the lens to be designed is a progressive power lens or an aspherical lens. Additionally, the eyeglass-lens design is to determine lens design information by controlling, for example, the transmittance of each wavelength that passes through the lens when the lens to be designed is a color lens. This color lens is not limited to a dye lens, and a reflection characteristic on the lens surface may be changed, or the absorption performance of the wavelength of an ultraviolet region or of a near-infrared region may be changed, or the property of a lens material, e.g., the Abbe number relative to color dispersion may be changed. The common feature is to perform lens design with respect to a to-be-designed object whose optical performance value, such as refractive power, an image formation state on the retina, spectral transmittance, or an Abbe number, can be calculated concerning a beam of light passing through the lens, and therefore that is not limited to these.

For example, concerning two or more kinds of to-be-evaluated lenses, an objective evaluation value of visual perception through each lens is calculated by use of the eyeglass-lens evaluation method, and, as a result, a difference in the optical performance value is obtained between one of the to-be-evaluated lenses that is highest in the evaluation and the remaining to-be-evaluated lens, and a new reference to-be-evaluated lens is designed as a new design target value obtained by adding a part of the difference to the optical performance value of the to-be-evaluated lens highest in the evaluation. Concerning a plurality of to-be-evaluated lenses including the new reference to-be-evaluated lens and the to-be-evaluated lens highest in the evaluation, it is possible to narrow the design by repeatedly performing an objective evaluation of visual perception by use of the aforementioned eyeglass-lens evaluation method.

Effects of the Invention

According to the present invention, it is possible to objectively evaluate average visual perception during a comparatively long time when a subject views an object through an eyeglass lens to be evaluated, a time-dependent change in visual perception, visual perception when the subject views an object with both eyes, and the balance of visual perception, and it is possible to design a suitable lens based on that evaluation. Additionally, when a characteristic of visual perception of the subject through the lens is calculated as a numerical value, it is possible to design a lens suitable for the subject based on information on that value.

DESCRIPTION OF EMBODIMENTS

Concrete embodiments of the present invention will be hereinafter described with reference to the drawings.

Embodiment 1

1. Experimental Conditions and Brain Activity Recording

Figure 1:
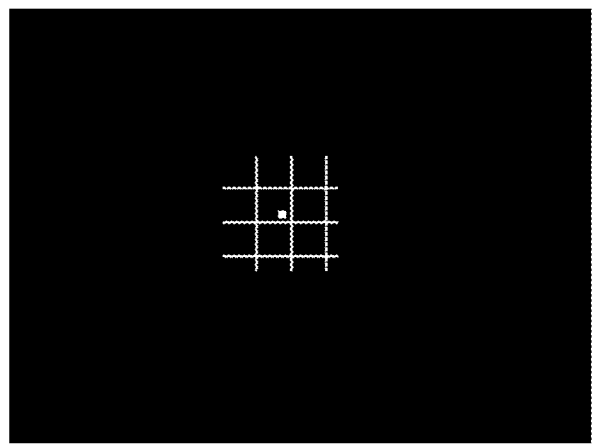
FIG. 1 A front view of an example of a fixation point and a visual stimulus object in Embodiment 1.
Figure 1:
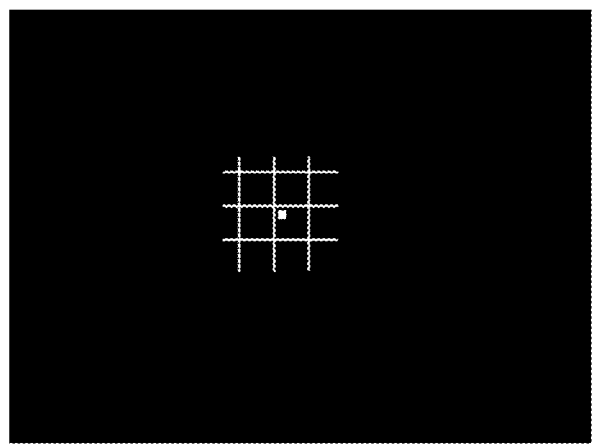

A fixation point is displayed frontally at a visual distance of two meters, and latticed images shown in (a) and (b) of FIG. 1 are alternately displayed with a 66.67-ms (millisecond) period without a blank-display interval of time. Although (a) of FIG. 1 and (b) of FIG. 1 are mutually different figures, these are very close to each other in the arranged shape of the latticed figure, and are the same in brightness and color of its entire image, and hence are images of visual stimulus objects that give the same stimulus to the low-level visual cortex of the cerebrum. These visual stimulus objects have the same brightness in (a) and (b), and hence are visual stimuli that induce neuron activities in the low-level visual cortex of the cerebrum when switching is performed between the images. Its period is 66.67 ms, and therefore periodic brain activities are induced in a steady state of 15 Hz. Each image is displayed with this period without a blank display interval of time for 90 seconds per lens condition while alternately performing switching between the images. The image has a visual angle of 8.6 degrees×8.6 degrees in size. The fixation point is actually displayed in red. A subject "A" is allowed to wear eyeglasses that have regular diopter power and that are in everyday use, and is allowed to wear eyeglasses having a load of S+4D, a load of S+2D, a load of S+1D, and a load of S+0.5D that are imposed to the regular diopter power (S+0D), and is instructed to gaze at the fixation point, thus recording brain activities at that time by use of a 306-channel magnetoencephalograph (Vector-view, ELECTA Neuromag). The 306-channel magnetoencephalograph includes 102 channels of magnetometers each of which serves as a magnetic sensor disposed in a helmet-shaped main body in a dispersion manner and 102 pairs of (204 channels of) gradiometers. The 306-channel magnetoencephalograph is capable of measuring a change in magnetic field caused by subject's brain activity by allowing the subject to put its main body on the head of the subject. A recording situation of brain activities is shown in, for example, FIG. 2.

2. Brain Activity Analysis

Figure 2:
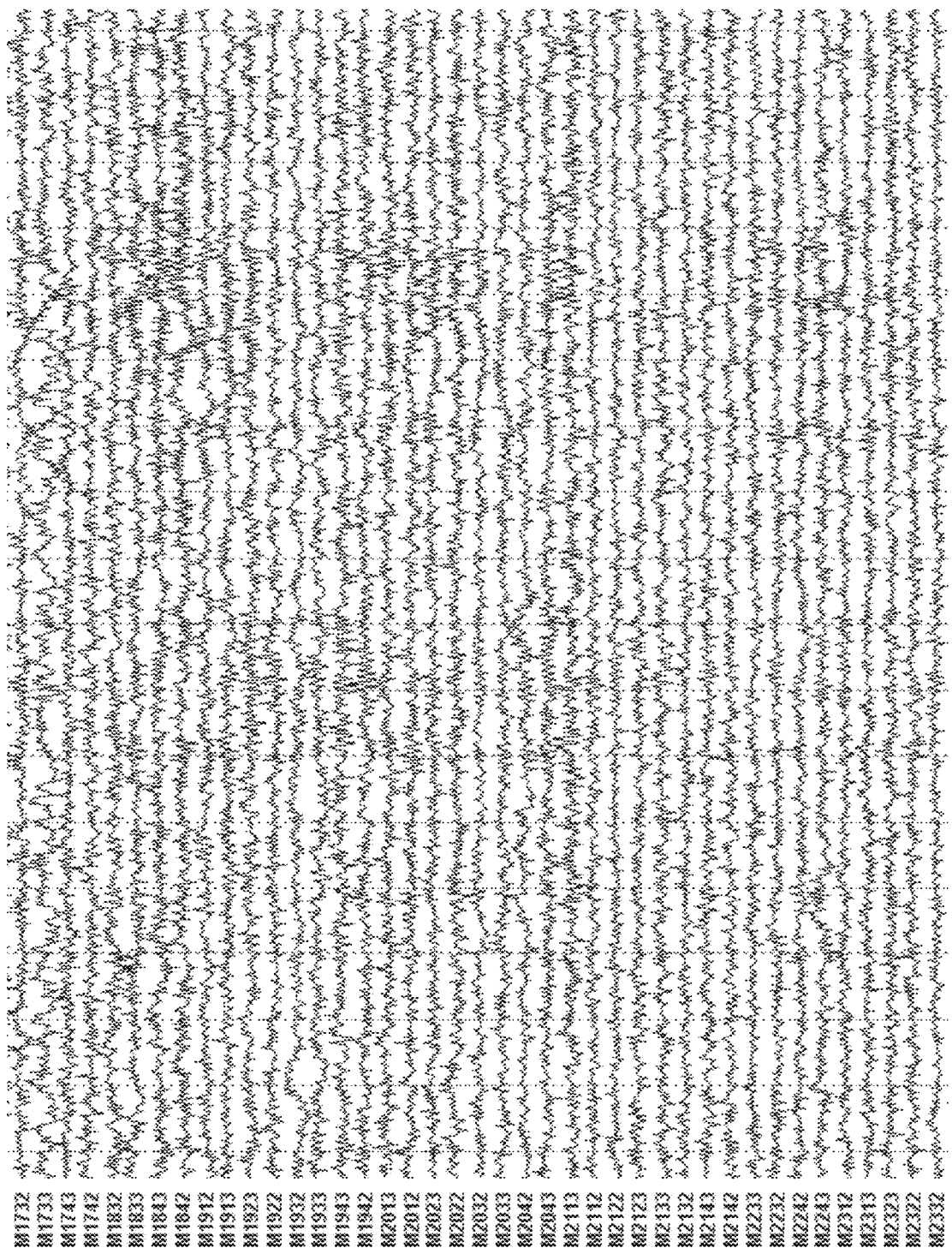
FIG. 2 A descriptive view to describe a situation in which waveforms of electrical signals of brain activities, which have not yet been analyzed, are recorded.

An analysis window that is used for analysis is set from waveforms of the brain activities recorded as in FIG. 2. Embodiment 1 is an example in which a period of 64 seconds, which ranges from 10 seconds after the start of measurement to 74 seconds after the start of measurement among 90 seconds during which measurement is performed, is set as an analysis window. 102 channels of magnetometers among 306 channels of magnetoencephalographic sensors are set as not being analyzed, and, from a record result of 204 channels (102 pairs) of gradiometers, Fast Fourier Transform (FFT) was performed concerning the waveforms included in the analysis window of 64 seconds with respect to each channel so as to be converted into a relationship between the frequency and the power value.

3. Result

Figure 3:
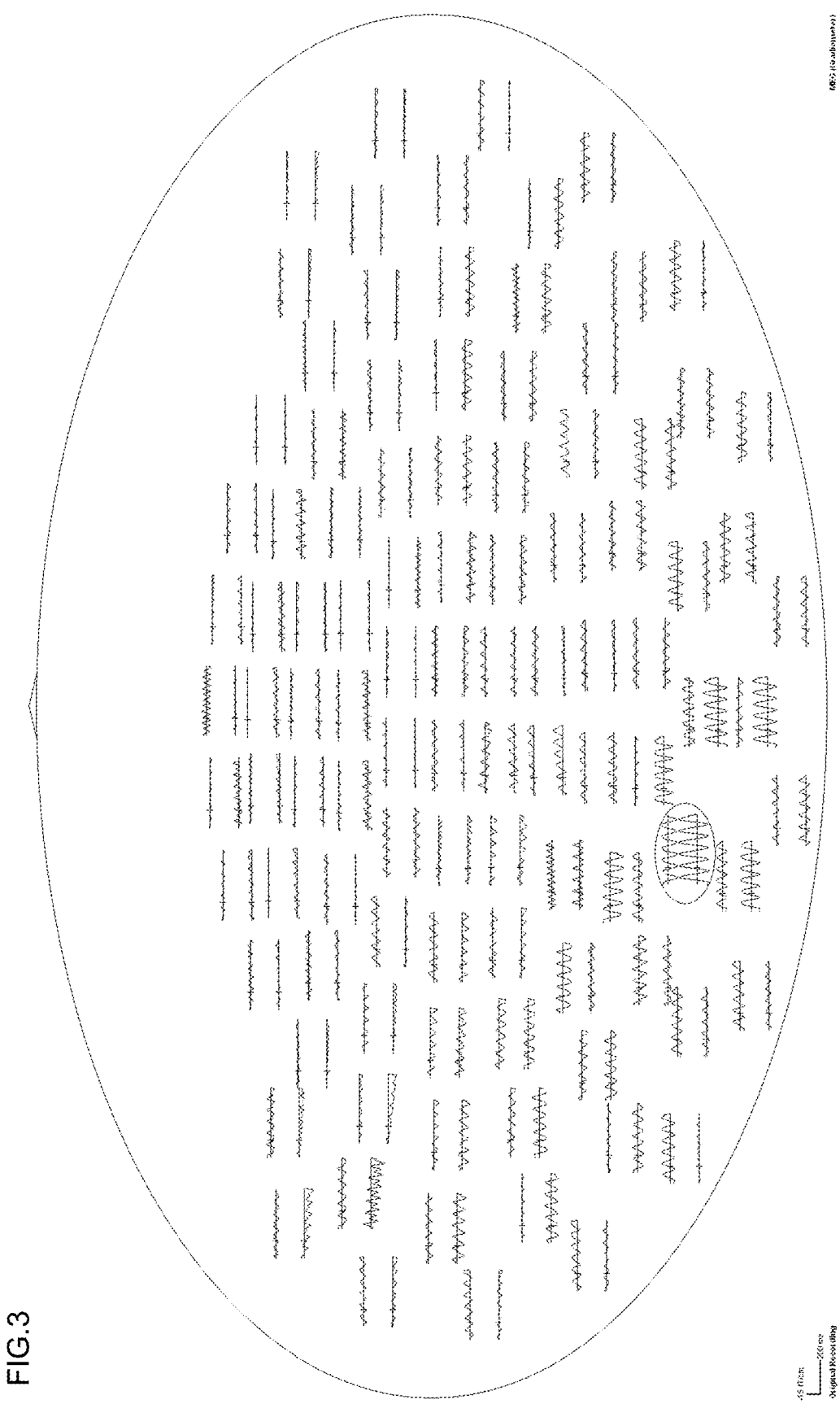
FIG. 3 A view showing an example of a measurement result in which each measurement position (gradiometer) of the brain in Embodiment 1 and an arithmetic average waveform of a change in obtained magnetic flux density are disposed in correlation with each other. A gradiometer pair consisting of M1922 and M1923 is circled in FIG. 3.

FIG. 3 shows a result in which the time when the images of Embodiment 1 were presented was defined as 0 seconds and in which arithmetic averaging from −100 milliseconds to +300 milliseconds was performed. It is understood that large brain activities are observed near the primary visual cortex at the position of a round mark of FIG. 3 (M1922 and M1923) and that periodic brain activities are observed. M1922 and M1923 denote name codes of gradiometers, respectively, showing the measurement position that is the position of the round mark. Although the arithmetic average waveform is not necessarily indispensable in the measurement and in the analysis of the present embodiment, it is possible to ascertain whether a periodic brain activity is induced.

Figure 4:
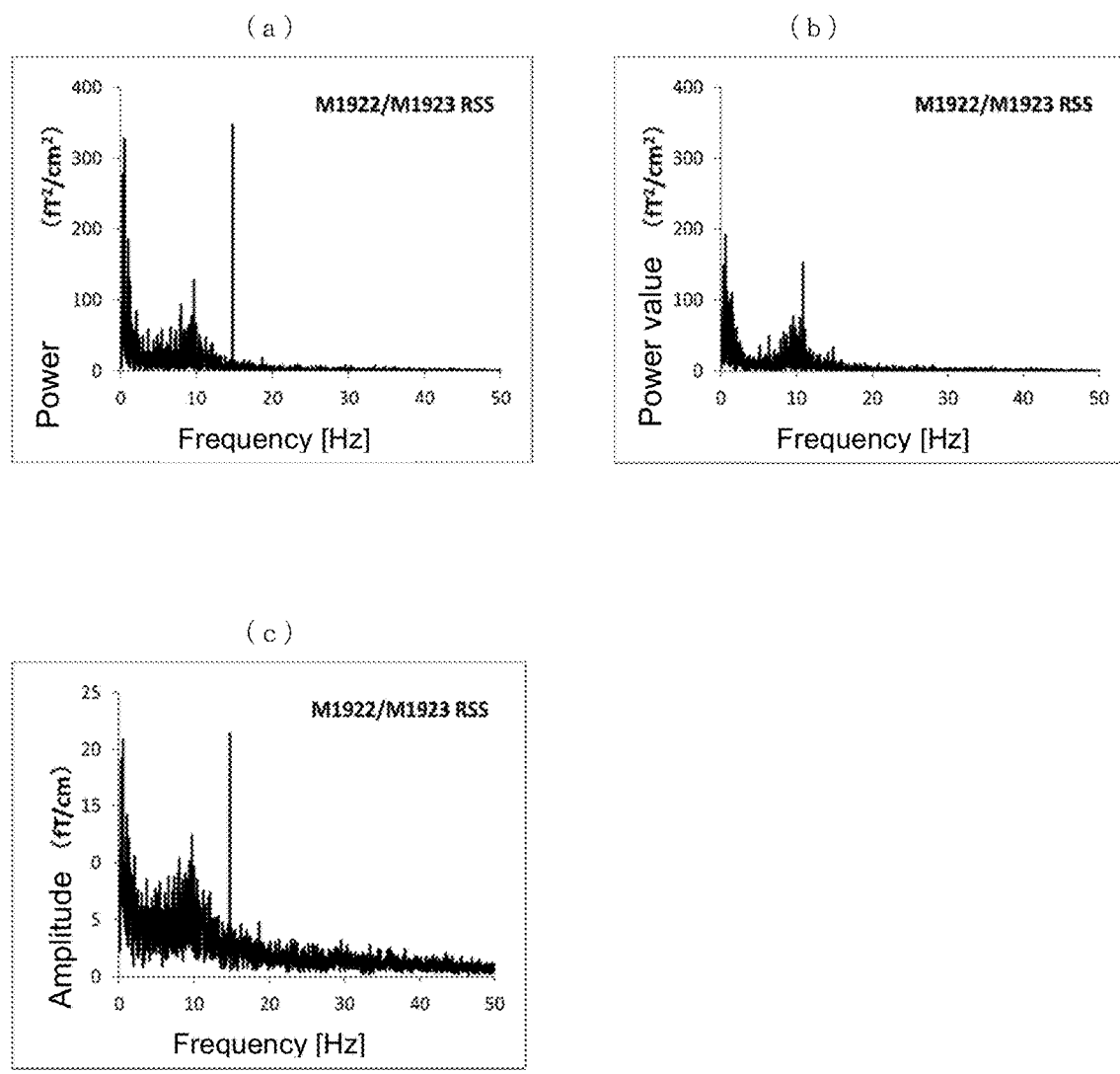
FIG. 4 (a) is a graph showing a relationship between the root-sum-square value (RSS value) of the power value of a gradiometer pair and the frequency when the load diopter power is S+0D, and (b) is, likewise, a graph showing a relationship between the root-sum-square value (RSS value) of the power value of a gradiometer pair and the frequency when the load diopter power is S+2D, and (c) is a graph showing a relationship between the root-sum-square value (RSS value) of the amplitude of a gradiometer pair and the frequency when the load diopter power is S+0D.

As an example, FIG. 4 shows graphs of a relationship between the root-sum-square (RSS) of the power value of a gradiometer pair of M1922 and M1923 showing the largest brain activity near the visual cortex and the frequency when two kinds of lenses of S+0D (no load) and S+2D are loaded to the regular diopter power of a subject "A." This result is an evaluation result of average visual perception of the analysis window of 64 seconds used for analysis. As shown in (a) of FIG. 4, when the load diopter power is S+0D, brain activity having high strength is observed at 15 Hz, and, as shown in (b) of FIG. 4, when the load diopter power is S+2D, its activity becomes remarkably small, and the size of the power value is 7% when the load diopter power is S+2D with respect to the size of the power value shown when the load diopter power is S+0D. In other words, it is understood that, in the subject "A," a lens having a load diopter power of S+0D is more suitable. Additionally, as a characteristic of the visual perception of the subject "A," it is understood that, when S+2D is loaded, i.e., when an image formation state on the retina is defocused by S+2D, the brain reaction becomes smaller by 93% than a state having no load (S+0D). Here, for example, in another subject B, if the brain reaction becomes smaller by 50% when S+2D is loaded to the regular diopter power than when no load is imposed, it is understood that the subject "A" is characterized by being susceptible to the defocus of an image caused by a spherical power error (load of S+2D) whereas the subject B is characterized by being insusceptible to the defocus of an image caused by a spherical power error (load of S+2D). Additionally, an α wave occurs in 8 to 13 Hz at this time, and therefore it is understood that it is preferable to use a range of 4 to 7 Hz that does not coincide with the α wave or a range of 14 Hz to 60 Hz when a brain reaction that uses frequency analysis is evaluated as in the present case. Additionally, particularly a range of 14 to 19 Hz is advantageous because it enables the measurement of a strong reaction as in (a) of FIG. 4. Additionally, although (c) of FIG. 4 shows a relationship between the amplitude and the frequency when the load diopter power is S+0D, the activity of 15 Hz is observed in this way even if the amplitude, not the power value, is used. Here, in relationships among the brain activity, the amplitude, and the power value based on background brain waves that center on the range of 8 to 13 Hz, it is understood that the use of the power value makes a difference thereamong larger than the use of the amplitude, and makes it easier to measure a targeted periodic brain activity.

Figure 5:
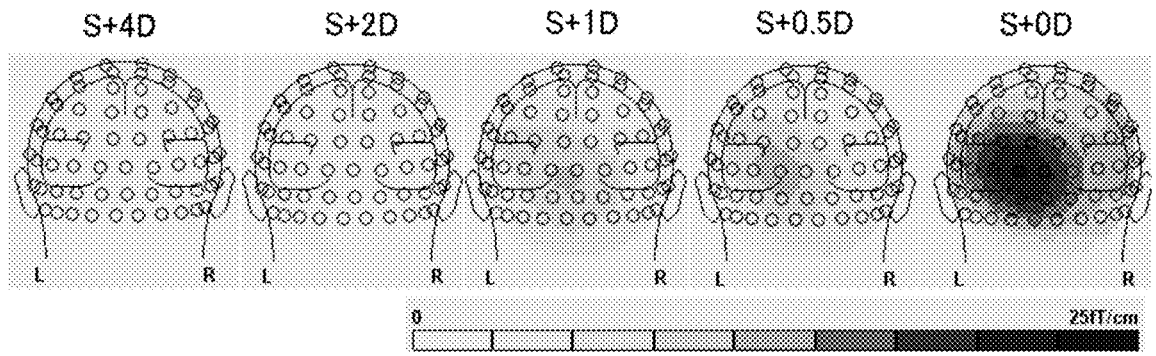
FIG. 5 An on-scalp distribution view in which the load diopter power in Embodiment 1 and a brain activity amplitude (fT/cm) of 15 Hz are projected to the back side of the head.

FIG. 5 shows a distribution view of the amplitude on the scalp of 15 Hz-activity depending on the load diopter power of the subject "A." As shown here, the brain reaction increases in proportion to a reduction in the load diopter power. Additionally, the amplitude of the brain activity rapidly falls even when the load diopter power is 0.5D, and therefore the method of the present invention is characterized by having very high sensitivity with respect to a diopter power error.

Embodiment 2

Embodiment 2 is an example in which the analysis window is set to be 8 seconds, and a comparison between two progressive power lenses is made concerning a time-dependent change in visual perception by continuously moving the analysis window while being overlapped.

1. Experimental Conditions and Brain Activity Recording

A fixation point was presented at a secondary position of eye twenty degrees below the front at a visual distance of 80 cm, and the subject B was allowed to wear a progressive power lens A and a progressive power lens B and is instructed to gaze at the fixation point, and, in the same way as in FIG. 1, the visual stimulus object that induces periodic brain activity was displayed for 60 seconds while alternately performing the switching between the images with a 66.67-millisecond period (with a frequency of 15 Hz) without a blank display interval of time. The brain activity at this time was measured by the magnetoencephalograph.

2. Brain Activity Analysis

The analysis window is set to be eight seconds when the waveform of the recorded brain activity is analyzed. First, measurement data at ±4 seconds that center on 8 seconds thereafter is selected, i.e., data at four seconds to twelve seconds after the stimulus object starts to be presented is selected, and, in the same way as in Embodiment 1, Fast Fourier Transform is performed with respect to the measured waveform of each gradiometer, and a channel in which the power value of each gradiometer becomes the maximum is selected, and the power value at that time is recorded. Thereafter, the analysis window is moved for four seconds. In other words, ±4 seconds are selected centering on 12 seconds thereafter, and Fast Fourier Transform is performed with respect to the data, and the power value of a channel that has become the maximum value in the preceding analysis is recorded. Thereafter, ±4 seconds are selected centering on 16 seconds thereafter, and, in this manner, the analysis window is moved, and a change in the power value from 8 seconds to 48 seconds (in data used for analysis, from 4 seconds to 52 seconds) is obtained. In other words, data is overlapped every four seconds.

3. Result

Figure 6:
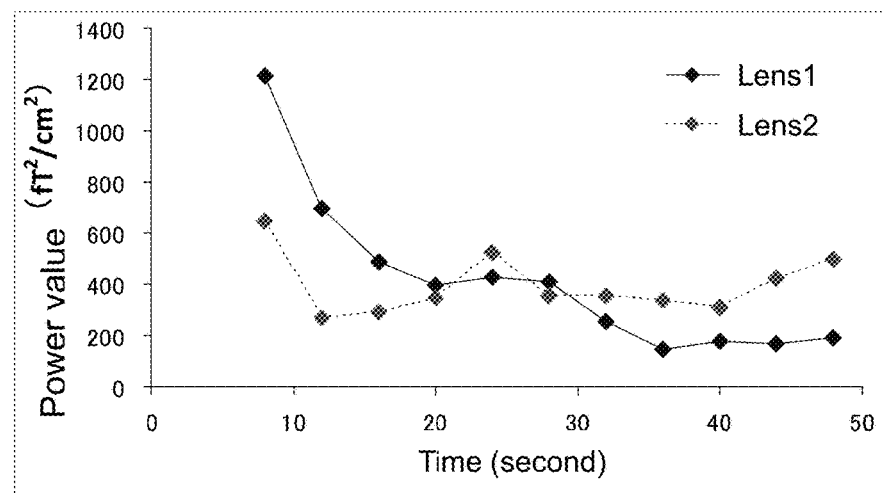
FIG. 6 A graph showing a relationship between a power value and a period of time that are measured when a subject wears a progressive power lens 1 and when the subject wears a progressive power lens 2 in Embodiment 2.

Changes in the frequency of 15 Hz relative to the measurement time of the power value of the progressive power lens 1 and of the power value of the progressive power lens 2 that have been thus obtained are shown in FIG. 6. Each point is an average value of ±4 seconds. In the solid line (progressive power lens 1) of FIG. 6, when measurement started, a large brain activity was observed by showing a power value of 1200 $fT^2/cm^2$, and, with the lapse of measuring time, the power value gradually fell and became 200 $fT^2/cm^2$ or less. On the other hand, in the progressive power 2 shown by the broken line, when measurement started, the power value was 600 $fT^2/cm^2$, and therefore the strength of the brain reaction was smaller than in the progressive power lens 1, and yet a fall in the power value hardly occurred with the lapse of measuring time, and a roughly equal power value was maintained even 48 seconds later. From this fact, it is possible to determine that, in the progressive power lens 1, the visual perception gradually falls although it is visually clear at the beginning, and, on the other hand, in the progressive power lens 2, more excellent visual perception than in the progressive power lens 1 is maintained in a concentrated state during about one minute although the initial visual perception is slightly inferior to that of the progressive power lens 1, and therefore the progressive power lens 2 is a lens that continues to have better visual perception for a long time than the progressive power lens 1. Here, although the present embodiment 2 was an example in which the analysis window was overlapped every four seconds, it is possible to employ the same analysis method even when the analysis window is overlapped, for example, every one second.

Embodiment 3

Embodiment 3 is to show that a periodic brain reaction induced in the present invention changes depending on how well an object is viewed with both eyes and is to objectively evaluate how well the object is viewed with both eyes by use of the brain reaction.

1. Experimental Conditions and Brain Activity Recording

A visual stimulus object that induces periodic brain activity with a 66.67-millisecond period (frequency of 15 Hz) was presented in front of a subject in the same way as in FIG. 1 shown in Embodiment 1, and ten subjects are allowed to wear eyeglasses that have regular diopter power and that are in everyday use, and a brain reaction was measured by the magnetoencephalograph when viewing with both eyes, when viewing with only a dominant eye while concealing a non-dominant eye, and when viewing with only a non-dominant eye while concealing a dominant eye. The stimulus period of time was set to be 64 seconds.

<Analysis>

The analysis window was set to be 32 seconds, thereafter Fast Fourier Transform was applied to the recorded first half and to the recorded latter half of 64 seconds, thereafter a gradiometer pair near the visual cortex in which the RSS of the power value in the frequency of 15 Hz becomes the maximum was selected with respect to each subject, thereafter the power value of the RSS was recorded, and the average of the power value of the first half and that of the power value of the latter half were calculated.

<Result>

Figure 7:
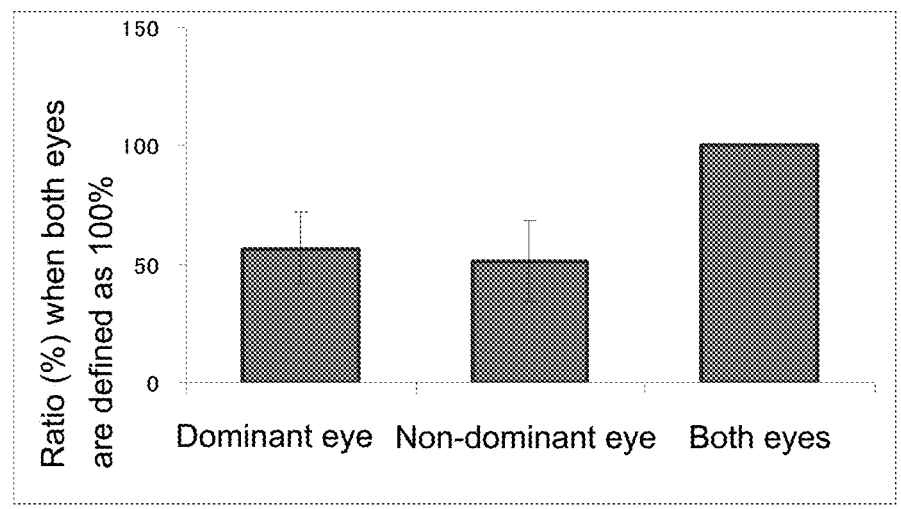
FIG. 7 A graph showing the ratio between a dominant eye and a non-dominant eye on the supposition that the root-sum-square value (RSS value) of a power value with both eyes measured with respect to a subject is 100% in Embodiment 3.

The power value of the dominant eye and the power value of the non-dominant eye were converted so as to become 100% when viewing with both eyes with respect to each subject, and the average value of all subjects was calculated. Its result is shown in FIG. 7. When viewing the object with both eyes as shown here, the brain reaction is observed about twice as strong as when viewing it with the single eye. As thus described, the use of the present invention makes it possible to objectively measure how well the object is viewed with both eyes.

Embodiment 4

Embodiment 4 relates to a method for measuring the balance of visual perception of both eyes.

1. Experimental Conditions and Brain Activity Recording

The visual distance was set at 1.5 m, and a fixation point was presented at the front, which is the primary position of eye, for five seconds, and then the fixation point is moved to the tertiary position of eye that is 18 degrees rightwardly and 18 degrees downwardly, and the same visual stimulus object as in FIG. 1 shown in Embodiment 1 that induces periodic brain activity with a 66.67-millisecond period (frequency of 15 Hz) was presented for 40 seconds behind the fixation point. Subsequently, the fixation point was presented at the front (primary position of eye) for 5 seconds, and then is moved 18 degrees leftwardly and 18 degrees downwardly, and a visual stimulus object was presented, and the brain activity was measured by the magnetoencephalograph in the same way as above. A subject was instructed to continue gazing at the fixation point only by the sight line. Load diopter powers, i.e., S+4D, S+2D, S+1D, S+0D, S−1D, S−2D, and S−4D are given to either the dominant eye or the non-dominant eye of a subject C in addition to the regular diopter power of the subject, and the subject is allowed to wear an eyeglass lens having the regular diopter power for the remaining eye.

2. Analysis

The analysis window was set to be 32 seconds, and Fast Fourier Transform was applied to data of 4 to 36 seconds after the stimulus was presented among 40 seconds spent for measurement, and the average value of the RSS of the power value in the frequency of 15 Hz at two measurement positions (lower-right and lower-left) was employed as an evaluation result of the lens.

3. Result

Figure 8:
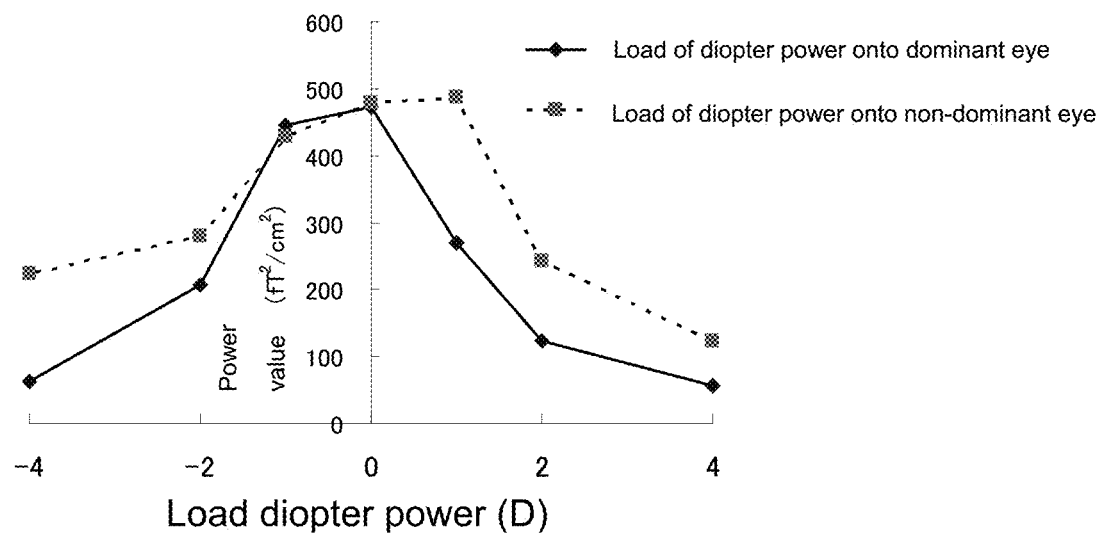
FIG. 8 A graph showing a relationship between the root-sum-square (RSS) of a power value with both eyes and the load of diopter power when the load of diopter power is given to the dominant eye and to the non-dominant eye measured with respect to a subject in Embodiment 4.
Figure 15:
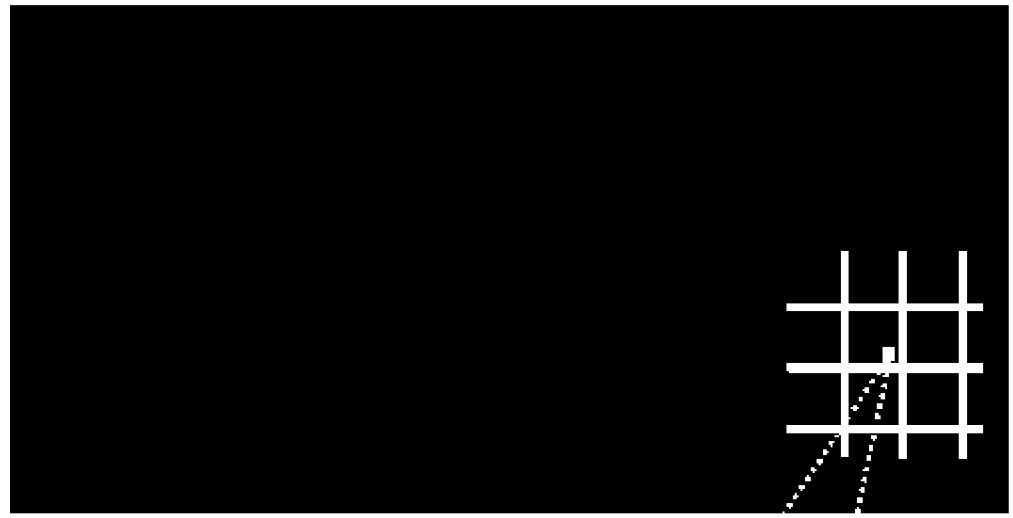
FIG. 15 A descriptive view to describe a transmission position on a lens when a fixation point and a visual stimulus object are viewed by both eyes at a secondary position of eye or a tertiary position of eye.
Figure 15:
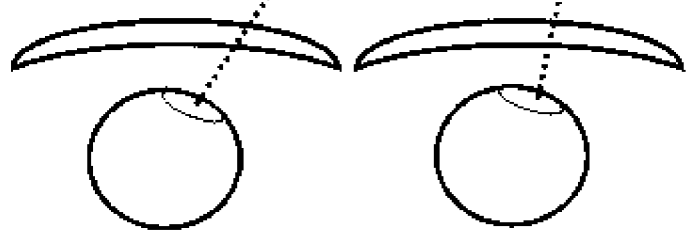

The result of the subject C is shown in FIG. 8. The solid line shows a case in which diopter power was loaded only to the dominant eye, whereas the broken line shows a case in which diopter power was loaded only to the non-dominant eye. As shown in FIG. 8, a change in the brain reaction (magnitude of the power value) occurs between a case in which it was loaded to the dominant eye and a case in which it was loaded to the non-dominant eye even if the load diopter power is the same in both cases, and therefore, in the subject C, the visual perception of the dominant eye and that of the non-dominant eye differ from each other, thus making it possible to achieve quantification in the brain reaction. As thus described, according to the measurement technique of the present invention, it is possible to objectively evaluate the balance of visual perception by a brain reaction even if there is a delicate case, such as a case in which a difference in visual perception occurs between the right and left eyes. The visual perception of the right eye and that of the left eye become different from each other, for example, when an object is viewed through a lateral part of the progressive lens with both eyes as shown in FIG. 15, and therefore it can be said that the technique of the present invention is effective for lens evaluation and for lens design in such a case. Additionally, as a characteristic of visual perception, it is understood that, in the subject C, the importance of the dominant eye is higher than the non-dominant eye, and the fall of the brain reaction (power value) is comparatively small even if the visual perception of the non-dominant eye becomes worse, and, if the visual perception of the dominant eye becomes worse, the brain reaction rapidly falls, and the visual perception becomes worse when viewing with both eyes. Additionally, it is understood that more desirable diopter power is obtained by adjusting the diopter power of the non-dominant eye slightly at the minus side. As thus described, the use of the present invention makes it possible to evaluate whether the balance of visual perception with both eyes of a subject is appropriate through objective measurement.

Embodiment 5

Embodiment 5 is a method for objectively evaluating visual perception that changes depending on the axial direction of astigmatism. In addition, this shows an example in which a fixation point is not displayed during measurement.

1. Experimental Conditions and Brain Activity Recording

Figure 9:
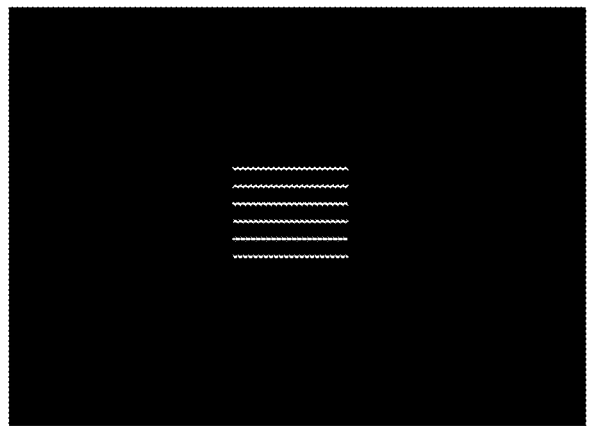
FIG. 9 A front view of an example of a visual stimulus object consisting of a plurality of line segments at which a fixation point is not displayed in Embodiment 5.
Figure 9:
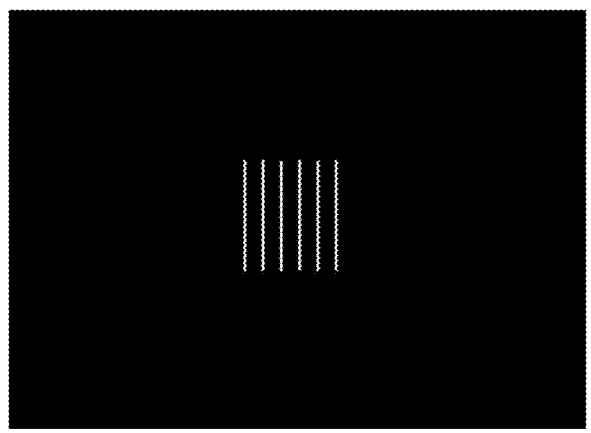

The visual distance was set at 80 cm, and a fixation point was presented at the front, which is the primary position of eye, for five seconds, and was then moved to a 25-degree rightward position (secondary position of eye), and was erased, and then two images shown in FIG. 9 that are visual stimulus objects that induce periodic brain activity were alternately displayed for 40 seconds so that one image has a 66.67-millisecond period (frequency of 15 Hz) in the display time. In other words, although the position of the fixation point is indicated to a subject, only a stimulus image is displayed without displaying the fixation point during measurement. In a case in which the subject is allowed to wear a spherical lens 1 having S−5.00D for the right eye and S−4.00D C−1.00D AX180 for the left eye that are regular diopter powers and in a case in which the subject is allowed to wear an aspherical lens 2 having the same diopter power, the subject was instructed to gaze at a place at which the fixation point was located to the last moment, and the brain activity at that time was measured by the magnetoencephalograph. The reason why the fixation point is not displayed during measurement is that it is supposed that a situation having difficulty in gazing occurs, e.g., it is supposed that a child is a subject or that a person having difficulty in a gazing act without fixing the sight line exists. Additionally, herein, the spherical lens 1 and the aspherical lens 2 are the same in the diopter power at the center, and yet are different in lens design around the lens. The lens curve is 0.5 Curve in both lenses, and, in the spherical lens, comparatively large astigmatism occurs at its peripheral part, whereas in the aspherical lens, astigmatism is restrained from occurring. In other words, as a condition, in the spherical power, an astigmatic component occurs, and, in the aspherical lens, an astigmatic component is restrained from occurring. At this time, at the position of the secondary position of eye at which a visual stimulus object is presented, the axial degree of the astigmatic component that has occurred is 90 degrees, and a greatest meridian is in the horizontal direction whereas a least meridian is in the vertical direction.

2. Analysis

The analysis window was set to be 32 seconds, and Fast Fourier Transform was applied to data of 4 to 36 seconds after the stimulus was presented among 40 seconds spent for measurement, and a gradiometer in which the power value in the frequency of 15 Hz becomes the maximum near the visual cortex when wearing an aspherical lens was selected, and its power value was analyzed.

3. Result

Figure 10:
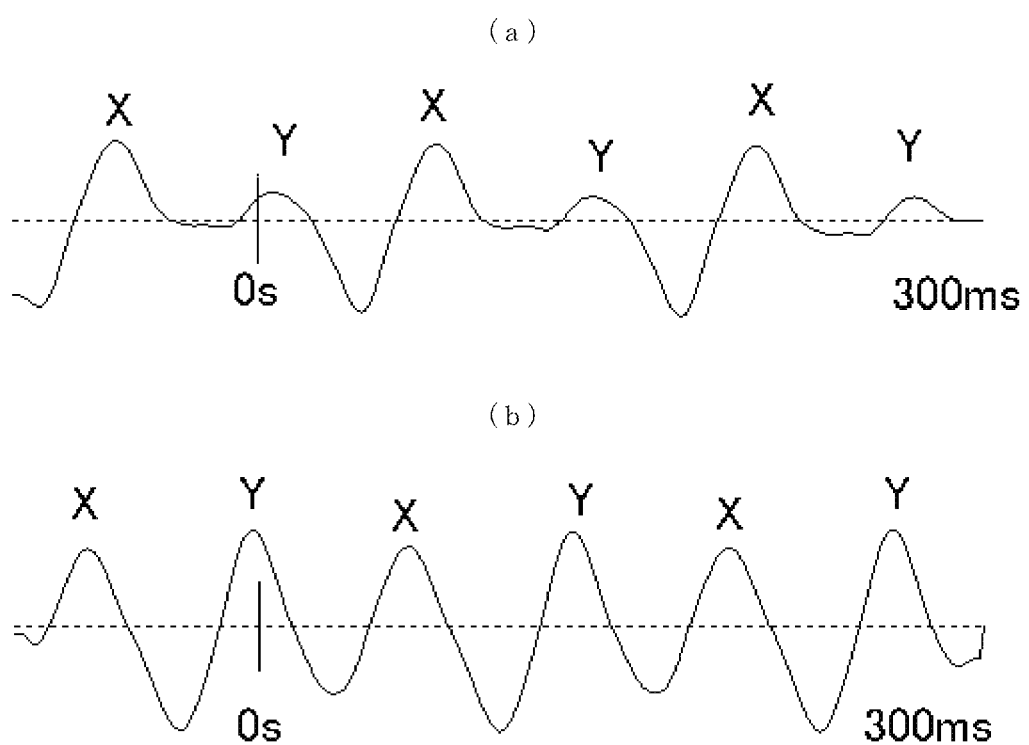
FIG. 10 In Embodiment 5, (a) is a graph of an arithmetic average waveform when a subject is allowed to wear a spherical lens large in astigmatism, whereas (b) is a graph of an arithmetic average waveform when the subject is allowed to wear an aspherical lens small in astigmatism.

To describe the organization of the brain reaction of the present embodiment, a description will be first given of waveforms ((a) and (b) of FIG. 10) of the arithmetic averaging of a maximum channel (M2122 channel) in the visual cortex in the middle of measurement. FIG. 10 here shows results obtained by performing arithmetic averaging from −100 milliseconds to 300 milliseconds on the supposition that the time when the stimulus image of (a) of FIG. 9 is displayed is 0 seconds. Herein, the letter X of (a) of FIG. 10 denotes the time when one, which is clearer than the other one, of the two line segment images having two directionalities, respectively, of FIG. 9 is viewed, and a strong reaction occurs in this image. The letter Y denotes the time when an image that is inferior in visual perception to the aforementioned image is viewed, and a small reaction occurs. In other words, the fact that visual perception changes depending on a relationship between the axial direction of an astigmatic component (astigmatism) and the directionalities of the line segments of (a) and (b) of FIG. 10 is reflected in the brain reaction. On the other hand, in (b) of FIG. 10, reactions having roughly the same level occur in X and Y although there is a slight difference therebetween, and therefore it is understood that the visual perceptions of the two images are roughly equally excellent. In other words, it is understood that the astigmatic component is small, and it is understood that the aspherical lens 2 is more desirable in visual perception.

Here, the analysis of the present invention that uses frequency analysis is performed with respect to measurement data that has not yet undergone arithmetic averaging as in FIG. 10. As a result, in the case of the spherical lens 1 ((a) of FIG. 10), the reaction of 15 Hz is hardly observed, and, instead, the reaction of 7.5 Hz comes to be observed. In the case of the aspherical lens 2 ((b) of FIG. 10), the reaction of 15 Hz is largely observed, and the reaction of 7.5 Hz is hardly observed. As thus described, in the evaluation of visual perception by the astigmatic component, the present embodiment 5 is characterized in that it is possible to measure the reaction as a brain reaction not only in the case of clear visual perception but also in the case of vague visual perception.

Embodiment 6

Embodiment 6 is to perform evaluation that reflects the absolute value of the amount of astigmatism (the absolute value of C diopter power) and a spherical power error without evaluating visual perception that depends on the axial direction of an astigmatic component, i.e., Embodiment 6 is an embodiment to evaluate how much an image is defocused by an astigmatic component and by a spherical power error although it is not used as an index in the direction of an astigmatic axis. This evaluation is important particularly in order to evaluate the visual perception of a lateral part of the progressive power lens or of a lens peripheral part of the aspherical lens. Additionally, this is important in order to evaluate a characteristic of user's visual perception by an astigmatic component and by a spherical power error.

Figure 11:
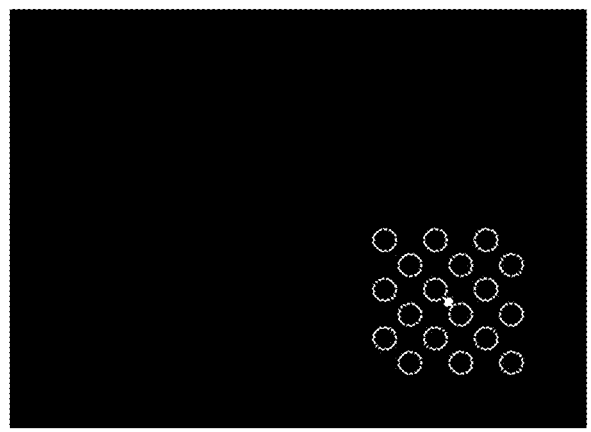
FIG. 11 A front view of an example of a visual stimulus object consisting of a fixation point and a plurality of non-directional figures (circles) in Embodiment 6.
Figure 11:
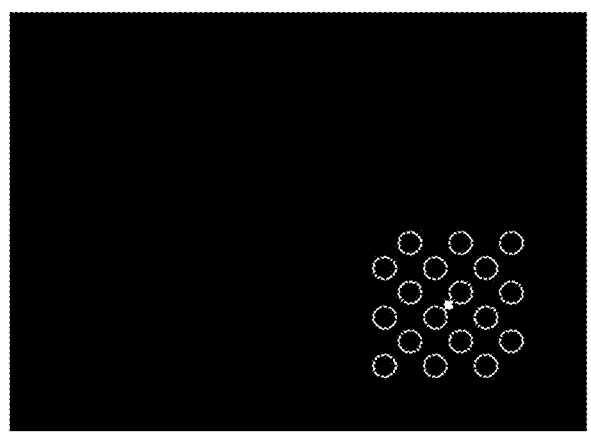

When a combination of line segments is used as in FIG. 1 and FIG. 9, line segments in a direction of clearer visual perception and line segments in a direction of vague visual perception appear in the axial direction of astigmatism, and the visual perception is influenced by the axial direction of astigmatism. Therefore, the visual perception is susceptible to the axial direction of residual astigmatism that is a difference between an astigmatic component of the eye of a subject and an astigmatic component when a sight line passes through a lens, and there is a case in which the influence not of the performance of a to-be-evaluated lens but of the axial direction of residual astigmatism of the subject is measured. To solve this problem, in Embodiment 6, a fixation point (square in the figure) was displayed at a tertiary position of eye as shown in (a) and (b) of FIG. 11, and two images each of which is composed of circles behind it and is equal in the brightness of the entire image were presented with a 66.67-millisecond period (frequency of 15 Hz), and the subject was allowed to gaze at the fixation point, and the brain activity at that time was measured.

A measuring operation having a measurement period of time of 20 seconds was performed twice (the fixation point was displayed at the lower right and the lower left), and the analysis window was set to be 16 seconds. The to-be-evaluated lens was a progressive power lens 1, a progressive power lens 2, and a progressive power lens 3, and Fast Fourier Transform was performed, and the RSS of the power value of 15 Hz of the maximum channel pair in the visual cortex was calculated, and evaluation values obtained by performing it twice (lower right and lower left) were averaged. As a result, in the subject D, it was 210 $fT^2/cm^2$ in the progressive power lens 1, it was 150 $fT^2/cm^2$ in the progressive power lens 2, and it was 360 $fT^2/cm^2$ in the progressive power lens 3, and hence it was determined that the aberration distribution of the progressive power lens 3 is excellent.

Embodiment 7

Embodiment 7 is concerned with one example of a design method for performing lens design according to the evaluation method of the present invention. Herein, a lens to be designed and to be evaluated is an inner-surface progressive power lens that has a progressive surface on the back surface.

In Embodiment 6, the result that the progressive power lens 3 is more excellent than the progressive power lenses 1 and 2 was obtained. What influences the brain reaction at that time is a case in which the sight line in viewing the fixation point of FIG. 11 passes through the lens. Therefore, coordinates in which the sight line in viewing the fixation point passes through lens-back surface coordinates are obtained, and optical performance values (average diopter power, astigmatism, etc.) of a predetermined range that centers on the coordinates (e.g., latticed data of 8 mm×8 mm and 1 mm step) are obtained with respect to the progressive power lenses 1 to 3. Concerning the thus obtained optical performance value data (1-mm-step latticed data) of the progressive power lenses 1 to 3, a difference between the optical performance value of the most highly evaluated progressive power lens 3 and that of the progressive power lens 1 and a difference between the optical performance value of the progressive power lens 3 and that of the progressive power lens 2 are calculated, and a data tendency is analyzed from two difference data obtained above, and common difference data is calculated. Half of the common difference data is added to the progressive power lens 3, and a new progressive power lens 4 is designed with a result obtained by addition as a design target value. Thereafter, concerning the progressive power lens 3, the progressive power lens 4, and a progressive power lens 5 for comparison (which is not necessarily required to be a new design), visual perception is repeatedly objectively evaluated by the magnetoencephalograph again, thus making it possible to improve the design by use of evaluation results of the present invention. It is possible to converge the design by repeatedly performing this evaluation.

Embodiment 8

Figure 12:
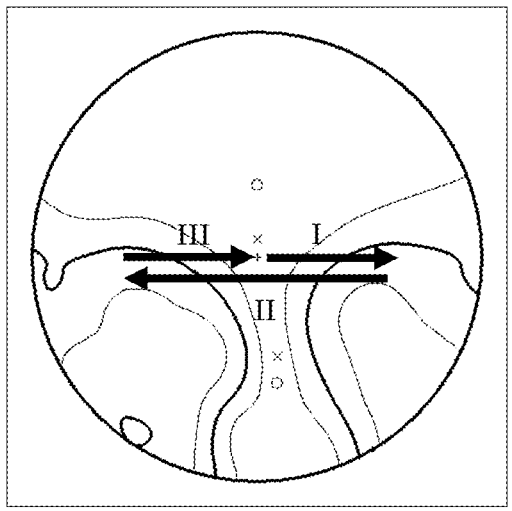
FIG. 12 A descriptive view to describe the movement trail of a sight line superposed on a progressive power lens on an astigmatism view from the back surface side of the progressive power lens in Embodiment 8.

Embodiment 8 is to make evaluation by moving a fixation point and an image behind the fixation point. The sight line is moved when eyeglass lenses are used in daily life, and therefore there is a need to objectively evaluate the easiness of viewing in moving the sight line. In FIG. 12, the movement trail of the sight line is expressed in coincidence with a lens. As shown in this figure, as an example, a case is described in which the sight line is moved from a viewing point slightly below the front toward the nose side (I of FIG. 12), and is then moved toward the ear side while reversing the sight line (II of FIG. 12), and is lastly returned from the ear side toward a point slightly below the front (III of FIG. 12).

1. Experimental Conditions and Brain Activity Recording

Figure 13:
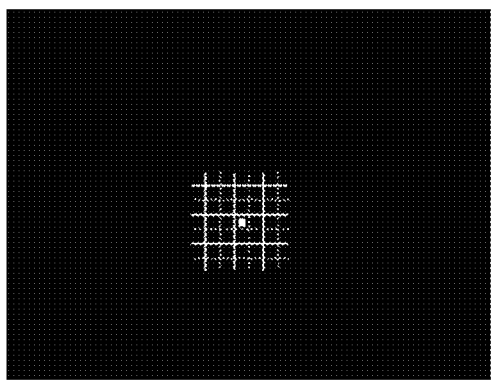
FIG. 13 (a) to (c) are descriptive views to describe a movement situation of a fixation point and a visual stimulus object corresponding to the movement trail of a sight line in the progressive power lens in Embodiment 8.
Figure 13:
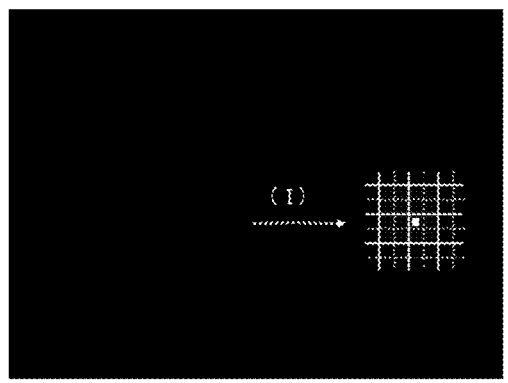
Figure 13:
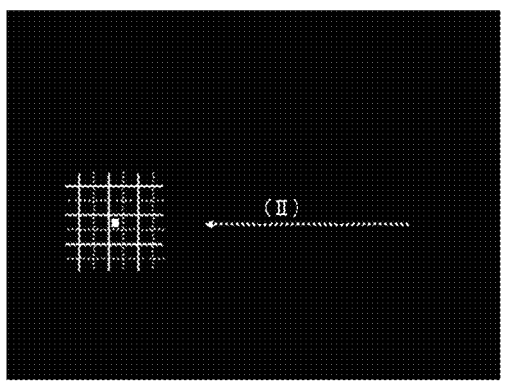

In a visual distance of 2 meters, a fixation point is presented slightly below the front, and (a) of FIG. 13 is displayed, and the fixation point is gradually moved toward the viewer's right-hand side while spending 10 seconds ((b) of FIG. 13). At that time, the image therebehind is also moved together, so that the positional relationship between the fixation point and the image is kept unchanged. Thereafter, the fixation point is smoothly moved from (b) of FIG. 13 to (c) of FIG. 13 while spending 20 seconds, and lastly the fixation point and the image are moved from (c) of FIG. 13 to (a) of FIG. 13 while spending 10 seconds. For descriptive convenience, in (a) to (c) of FIG. 13, two lattice figures to be alternately displayed are displayed so as to cross each other on one figure by means of the solid line and the broken line. The figures of (a) to (c) of FIG. 13 drawn by the solid line and the broken line are displayed while being alternately switched with a 66.67-millisecond period (frequency of 15 Hz). This arrangement allows the sight line to pass through the lens for the left eye in the manner of I→II→III of FIG. 12, and the visual perception starts to be gradually defocused from a clearly visible region (front), and the sight line reaches the nose side (sight-line movement of I), and then a clearly visible state is reached from the defocused state, and again a defocused state is reached, and the sight line reaches the ear side (sight-line movement of II). Lastly, a clearly visible state (front) is reached from the defocused state (nose side) (sight-line movement of III). As thus described, the subject is allowed to wear the progressive power lens, and the fixation point is moved, and the subject is instructed to gaze at the fixation point, and, as a result, it becomes possible to control the position of the sight line passing through the lens.

The subject was allowed to wear the progressive power lens 1 and the progressive power lens 2, and the image shown in FIG. 13 was continuously moved (40 seconds in total), and the brain activity at that time was recorded by the magnetoencephalograph.

2. Analysis

Analysis is performed in the same way as in the foregoing embodiments. If average visual perception is expected to be evaluated, the analysis window is set to be 32 seconds, and, if a time-dependent change in visual perception is expected to be evaluated, the analysis window is set to be 8 seconds, and is moved every four seconds. After the analysis window is set, Fast Fourier Transform is performed, and a channel that reaches the maximum power value in the visual cortex is selected, and the RSS of the power value of 15 Hz of a gradiometer pair including this channel is recorded.

3. Result

Although this arrangement results in a change in visual perception in the sight line of I→II→III of FIG. 12, i.e., clearly visible (front)→defocused (nose side)→clearly visible (front)→defocused (ear side)→(clearly visible), it becomes possible to make a comparative evaluation of visual perception in relation to the movement of the sight line of the progressive power lens 1 and that of the progressive power lens 2 by comparing power values in which measurement results have been subjected to frequency analysis.

Herein, for descriptive convenience, the position on the lens at which the sight line of the left eye passes through the lens for the left eye has been described with reference to FIG. 12 of Embodiment 8, and yet, in practice, it is important to allow the subject to view a moving fixation point with both eyes as shown in FIG. 15. Although coordinates of the sight line passing through the lens become different in the left and right eyes by allowing the subject to view the moving fixation point with both eyes, visual perception including the balance of visual perception of the right and left eyes is evaluated in the present embodiment. The relationship between the balance of visual perception of the right and left eyes and the RSS of the power value is described in the same way as in Embodiments 3 and 4.

Embodiment 9

Embodiment 9 shows a case in which blank display intervals of time are given although Embodiments 1 to 8 show a case in which blank display intervals of time are not given. There is a case in which the strength of a brain reaction is difficult to obtain depending on personal differences between subjects, and, in that case, it becomes possible to obtain brain reactions of most subjects, for example, by first allowing a subject to view a visual stimulus object that induces periodic brain activity without a blank display interval of time and then measuring it while using a visual stimulus object with blank display intervals of time if a targeted brain reaction is weak.

1. Experimental Conditions

This is an example in which images of (a) and (b) of FIG. 1 are alternately displayed in 166.66 milliseconds. When the visual distance is 2 m, the two images are alternately displayed in 166.66 milliseconds if blank display intervals of time are not given. If blank display intervals of time are given, (a) of FIG. 1 is displayed for 83.33 milliseconds, and then a blank image is given for 83.33 milliseconds (at this time, only the fixation point is displayed without displaying an image on the background), and then (b) of FIG. 1 is displayed for 83.33 milliseconds, and then a blank image is given. Therefore, the frequency by the repetition at this period is 6 Hz.

When a load diopter power of S+0D and a load diopter power of S+4D are given to eyeglasses having the regular diopter power worn by the subject E, the brain activity is measured by the magnetoencephalograph. Measurement was performed for 40 seconds.

2. Analysis

The analysis window was set to be 32 seconds, and Fast Fourier Transform was performed, and a channel that reaches the maximum power value in the visual cortex was selected, and the RSS of the power value of a gradiometer pair including the channel was calculated, and that power value was recorded.

3. Result

Figure 14:
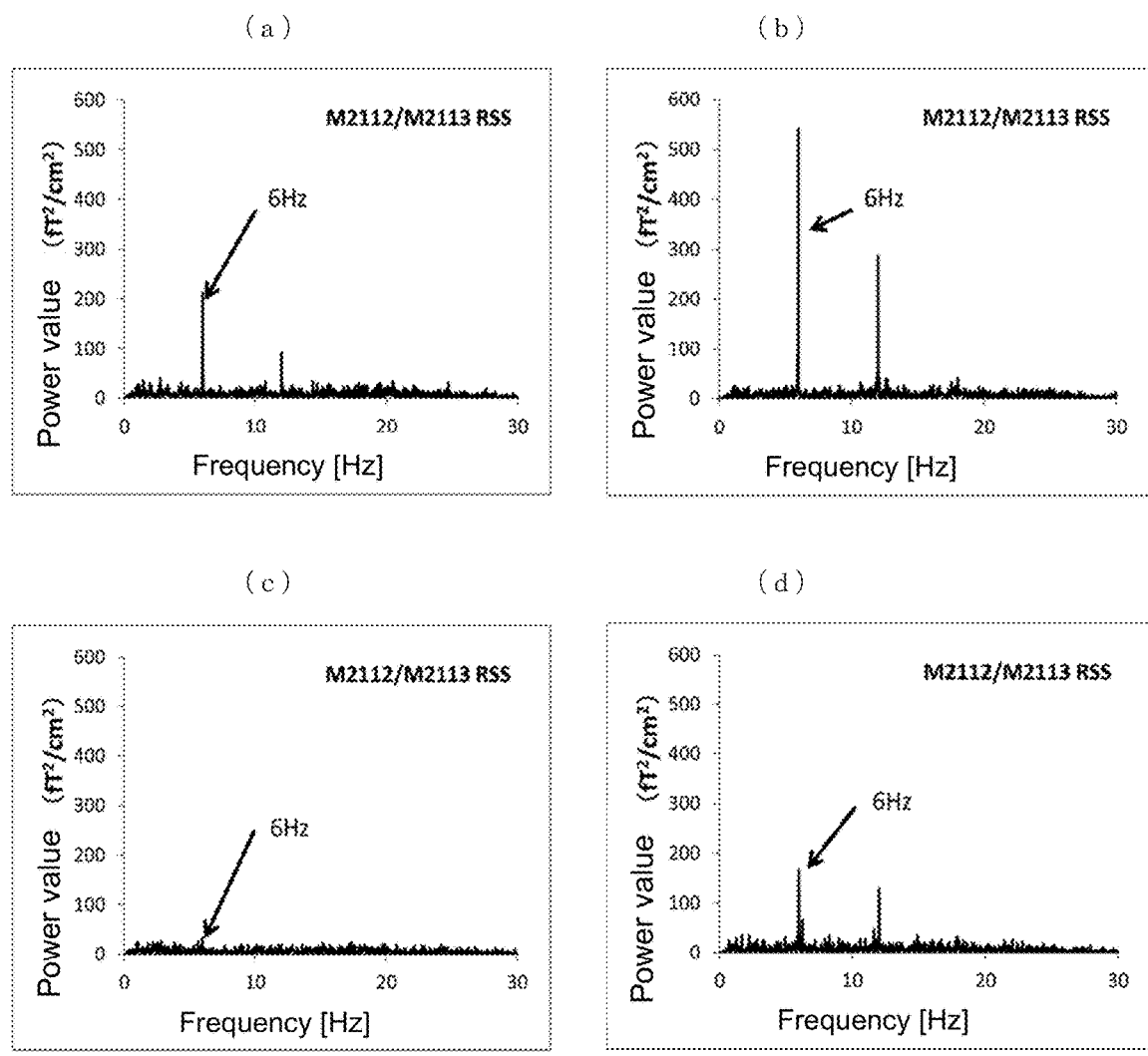
FIG. 14 In Embodiment 9, (a) is a graph showing a relationship between the root-sum-square value (RSS value) of a power value and the frequency when blank display intervals of time are not given in a load diopter power of S+0D, (b) is likewise the same graph when blank display intervals of time are given in a load diopter power of S+0D, (c) is the same graph when blank display intervals of time are not given in a load diopter power of S+4D, and (d) is likewise the same graph when blank display intervals of time are given in a load diopter power of S+4D.

In the load diopter power of S+0D, a stronger brain reaction of 6 Hz was observed in a case in which blank display intervals of time are given than in a case in which blank display intervals of time are not given ((a) and (b) of FIG. 14). On the other hand, in the load diopter power of S+4D, a targeted brain activity was buried in the brain activity of the background when blank display intervals of time were not given, whereas an activity of 6 Hz was obtained when blank display intervals of time were given even if the load diopter power is S+4D ((c) and (d) of FIG. 14). As thus described, when the strength of a brain reaction is difficult to obtain, the present embodiment is effective because it becomes possible to periodically generate a brightness-change stimulus by periodically giving a blank display interval of time of a stimulus image.

Embodiment 10

Embodiment 10 is concerned with one example of a method for evaluating visual perception through a lens by use of phases.

1. Experimental Conditions

The subject D is allowed to wear a progressive power lens of an astigmatism view shown in FIG. 12, and is instructed to continue viewing a fixation point. The fixation point is displayed at the front (primary position of eye) at a visual distance of 2 m, and latticed images shown in (a) and (b) of FIG. 1 are alternately displayed with a 66.67-millisecond period without a blank display interval of time. Thereafter, the fixation point is displayed at the diagonally lower right (tertiary position of eye), and the latticed images of (a) and (b) of FIG. 1 are displayed for 40 seconds therebehind. The brain reaction at that time is measured by the 306-channel magnetoencephalograph.

2. Analysis

The analysis window is set to be 32 seconds, and Fast Fourier Transform is performed, and the phase is calculated in a case in which the image is displayed at the primary position of eye and in a case in which the image is displayed at the tertiary position of eye. The phase is obtainable by calculation simultaneously with the amplitude and with the power value according to a technique, such as Fast Fourier Transform.

3. Result

The phase in viewing the front (primary position of eye) of the lens was 50 degrees, and the phase in viewing the diagonally lower part (tertiary position of eye) of the lens was 212 degrees, and it was ascertained that there is a delay of a phase of 162 degrees in the sight line of the tertiary position of eye in comparison with the primary position of eye. When the lens is a progressive power lens, an image is clearly viewed at the primary position of eye and an image is vaguely viewed at the tertiary position of eye owing to astigmatism, or curvature of field, or a difference between left and right images when viewing the image with both eyes, and therefore this phase delay denotes that this evaluated progressive power lens has greater difficulty in visual perception at the tertiary position of eye than at the primary position of eye. Therefore, the use of this phase slowness/fastness makes it possible to, for example, evaluate whether a desirable lens for the subject D is the progressive power lens 1 or the progressive power lens 2 or makes it possible to perform lens design based on evaluation results. Additionally, it becomes possible to evaluate a characteristic of the visual perception of the subject by making a comparison between the primary position of eye and the tertiary position of eye. For example, let it be supposed that, when the progressive power lens 1 is worn, a phase of 162 degrees is delayed at the tertiary position of eye in comparison with the primary position of eye in the subject D, whereas a phase of 100 degrees is delayed at the tertiary position of eye in comparison with the primary position of eye in the subject E. At this time, the subject D is larger in the amount of delay of the phase at the tertiary position of eye of the progressive power lens, and therefore it is possible to evaluate the characteristic of the visual perception of being susceptible to the influence of aberration that exists in a diagonally lower direction of the progressive power lens.

Figure 16:
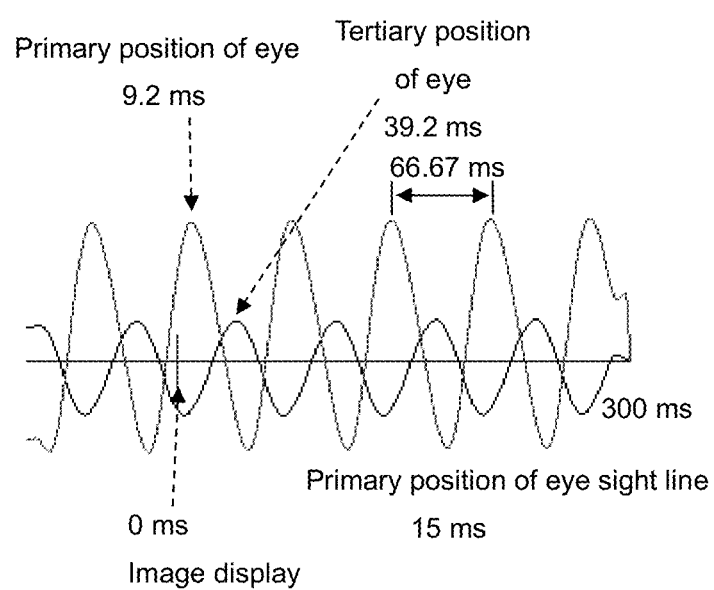
FIG. 16 Averaged waveforms of a gradiometer channel that has peaked in the visual cortex of the occipital lobe when the visual stimulus object is viewed by both eyes at the primary position of eye or the tertiary position of eye in Embodiment 10.

Here, in order to describe the phase, averaged waveforms of the gradiometer (M2112) showing the maximum reaction in the visual cortex are shown in FIG. 16. This is obtained such that the time when an image is presented is defined as 0 ms, and arithmetic addition is performed 600 times, and waveforms of a channel in which the strongest reaction in the visual cortex of the occipital lobe is obtained are selected from the waveforms of the entire head measured as in FIG. 3. As shown in FIG. 16, this is a brain reaction in a steady state of 15 Hz having a period of 66.67 ms both when viewing an object at the primary position of eye and when viewing an object at the tertiary position of eye. When viewing it at the tertiary position of eye, the brain reaction is later by 30 ms than at the primary position of eye, and the period is 66.67 ms, and therefore it is understood that there is a phase delay of 162 ms.

Here, it is understood by paying attention to the amplitude of FIG. 16 that, when viewing it at the primary position of eye, the amplitude is three times as large as when viewing it at the tertiary position of eye and that more comfortable visual perception is obtained at the primary position of eye than at the tertiary position of eye, and therefore it is understood that the lens performance can be evaluated by a combination of the amplitude and the phase. It becomes possible to have the expectation that the influence of a measurement noise or of a measurement error is able to be reduced by making evaluation by a combination of the amplitude and the phase or a combination of the power value and the phase as above, and therefore it is preferable to use a plurality of evaluation values concerning the same measurement. The averaged waveforms of FIG. 16 is formed by the addition of the duration of 40 seconds (600 times), and it is necessary to add somewhat many times, and therefore a measurement result of from a few seconds to tens of seconds is required in order to obtain a measurement value. On the other hand, when attention is paid to the phase delay, a phase is capable of being calculated by each analysis window, and therefore it becomes possible to evaluate visual perception during a very short time in real time by setting the analysis window to be, for example, 512 milliseconds.

Embodiment 11

Embodiment 11 is an example in which a user characteristic when a subject (a user) wears an eyeglass lens is evaluated by measuring a brain reaction when the subject is allowed to wear a lens for a specific evaluation. In this example, although the user characteristic is measured by a magnetoencephalograph placed in a laboratory, the brain reaction of the visual cortex measured by this magnetoencephalograph can be measured even by use of an electroencephalograph by disposing electrodes on the occipital lobe. Therefore, it is possible to measure it in the same way by use of the electroencephalograph in, for example, an optician's store.

1. Experimental Conditions and Brain Activity Recording

A fixation point is presented at the front at a visual distance of 100 cm, and the lattice figures of (a) and (b) of FIG. 1 are alternately displayed with a 66.67-millisecond period. Defocusing or distortion is loaded to the dominant eye and to the non-dominant eye of a subject by means of lenses under the conditions of condition A: no load to both eyes, condition B: a load to the dominant eye and no load to the non-dominant eye, condition C: a load to the non-dominant eye and no load to the dominant eye, and condition D: a load to both eyes, and the subject is allowed to gaze at the fixation point. For example, in order to load defocusing thereto by means of lenses, spherical power or the like is used as a loading lens. For example, in order to load distortion thereto by means of lenses, a progressive lens, such as S+0.00 ADD2.00 or astigmatic power, is used as a loading lens. The display period of time of a visual stimulus object is set to be 20 seconds, and the brain reaction is repeatedly measured while changing the conditions.

2. Analysis

The analysis window was set to be 16 seconds, and the power value of the brain activity of 15 Hz was calculated under each of the conditions A to D in the same way as in Embodiment 3.

3. Result

Figure 17:
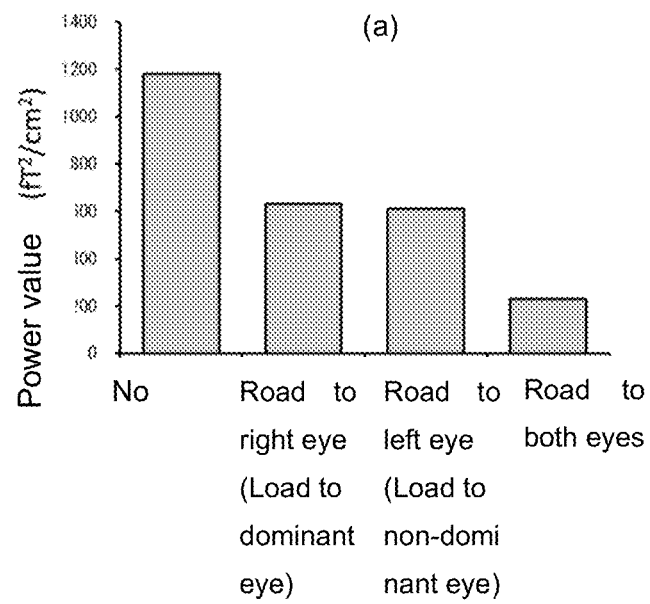
FIG. 17 Views of a comparison by a brain reaction between (a) visual perception when defocusing is loaded to the dominant eye and to the non-dominant eye of a subject E and (b) visual perception when distortion is loaded thereto in Embodiment 11.
Figure 17:
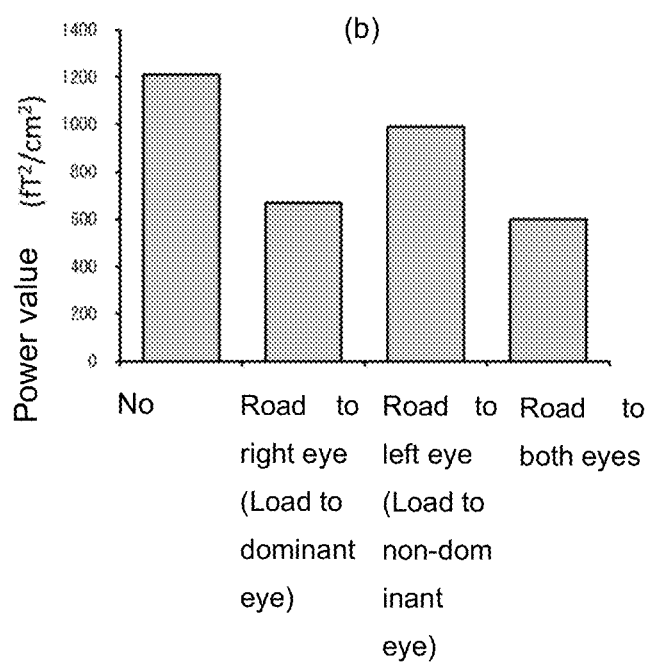
Figure 18:
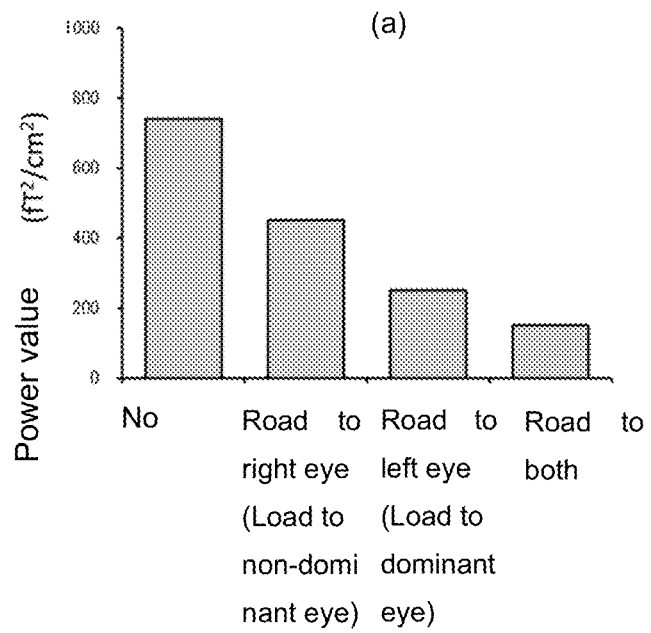
FIG. 18 Views of a comparison by a brain reaction between (a) visual perception when defocusing is loaded to the dominant eye and to the non-dominant eye of a subject F and (b) visual perception when distortion is loaded thereto in Embodiment 11.
Figure 18:
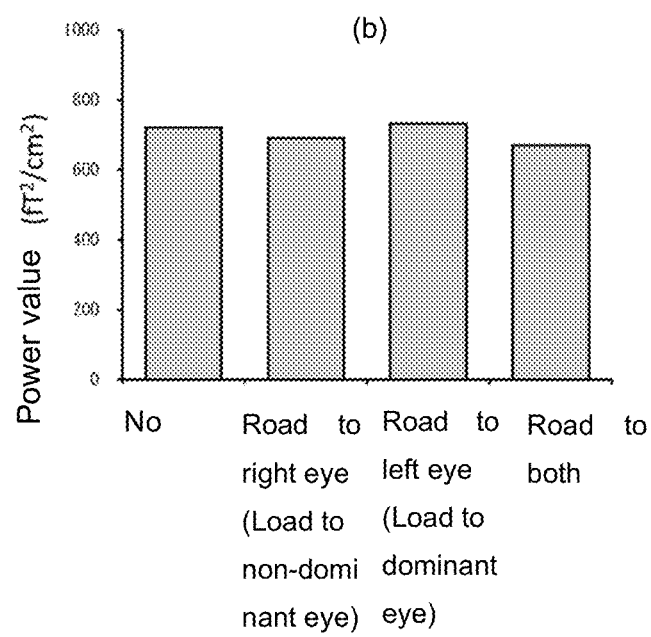

Here, results with respect to the subject E (whose right eye is a dominant eye) and with respect to the subject F (whose left eye is a dominant eye) are shown in FIG. 17 and FIG. 18.

First, in the subject E, when defocusing is loaded to a single eye of the subject E (i.e., when the single eye is brought into a defocused state), the strength of the brain reaction is approximately halved, and, when defocusing is loaded to both eyes, the strength of the brain reaction becomes about ⅙ as shown in (a) of FIG. 17. At this time, there is no difference between loading to the dominant eye and loading to the non-dominant eye. On the other hand, as shown in (b) of FIG. 17, when distortion is loaded to the dominant eye, the strength of the brain reaction is reduced approximately by half, and, when distortion is loaded to the non-dominant eye, the amount of decrease is half a case in which distortion is loaded to the dominant eye, and, when distortion is loaded to both eyes, the strength thereof is substantially the same as when distortion is loaded to the dominant eye. From these facts, it is understood that the subject E has the following characteristics.

Although there is no large difference between the dominant eye and the non-dominant eye with respect to defocusing, there is a difference in the brain reaction between the dominant eye and the non-dominant eye with respect to distortion.

When distortion is loaded to the right eye that is a dominant eye, the brain reaction largely falls.

Even when distortion is loaded to the left eye that is a non-dominant eye, the brain reaction does not easily fall.

When both eyes reach a defocused state, the brain reaction rapidly falls, and, when both eyes reach a distorted state, the brain reaction becomes as high as when the dominant eye reaches a distorted state.

Next, concerning the subject F, results obtained by performing the same measurement are shown in FIG. 18.

In the subject F, the strength of the brain reaction hardly changes even when distortion is loaded as shown in (b) of FIG. 18, and the brain reaction falls when defocusing is loaded particularly to the dominant eye as shown in (a) of FIG. 18. From these facts, it is understood that the subject F has the following characteristics.

The subject F is more susceptible to defocusing than distortion.

The brain reaction largely falls when the dominant eye reaches a defocused state.

As thus described, the use of the present invention makes it possible to measure how the dominant eye and the non-dominant eye of the user have characteristics of visual perception with respect to defocusing and distortion.

Embodiment 12

Embodiment 12 is an example in which characteristics of user's visual perception are measured and, based on information on the characteristics of the visual perception, lens design is carried out. Although a description is herein given of a case in which a lens is designed by measuring characteristics of the visual perception of a user with respect to defocusing, the lens design technique is not limited to this.

1. Measurement of User's Characteristics

A user is allowed to view visual stimulus objects shown in (a) and (b) of FIG. 1 that are the same as in Embodiment 1 in, for example, an optician's store, and a brain reaction is measured with an electroencephalograph. At this time, the user is allowed to wear a lens having diopter power (S+1D load condition) obtained by loading S+1D to diopter power adjusted for the user to preferably view a distant object, and is allowed to view a visual stimulus object for 20 seconds, and is then allowed to wear a lens having diopter power (S+0D load condition) adjusted for the user to preferably view a distant object, and is allowed to view the visual stimulus object for 20 seconds. Electrodes of the electroencephalograph are disposed at O1 and O2 in the international 10-20 electrode system, and a reference electrode is set up at the right ear, and a ground electrode is set up at the head vertex. The visual distance to the visual stimulus object is set at 5 m, and the visual angle is set at 4 degrees. Measured brain waves are analyzed by an application attached to a measuring device, and power values are obtained with respect to the S+1D load condition and the S+0D load condition, respectively. Furthermore, a defocusing characteristic of user's visual perception is calculated according to the equation: Defocusing Characteristic=(power value of the S+1D load condition)/(power value of the S+0D load condition). In this defocusing characteristic, if it is a large numerical value, the reduction of a brain reaction is small even when S+1D is loaded, and hence it is understood that the user has visual perception characterized in that the deterioration of visual perception caused by defocusing is small, and, on the other hand, if it is a small numerical value, it is understood that the user has visual perception characterized in that the deterioration of visual perception is liable to occur even if defocusing is slight. Here, let it be supposed that the defocusing index of the user E is calculated as 0.4.

2. Lens Design

Figure 19:
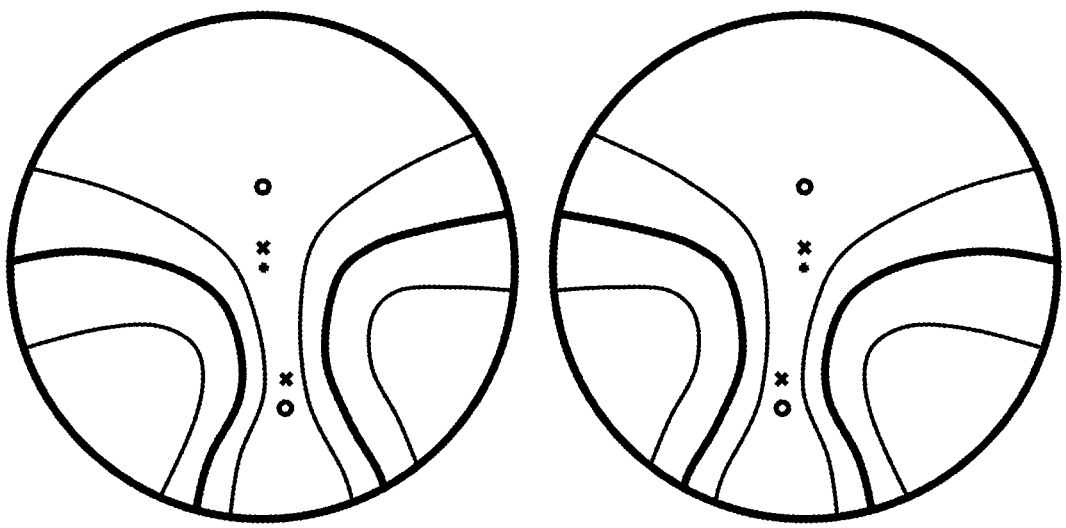
FIG. 19 (a) is an astigmatism view of conventional design for the right eye, whereas (b) is an astigmatism view of conventional design for the left eye.
Figure 20:
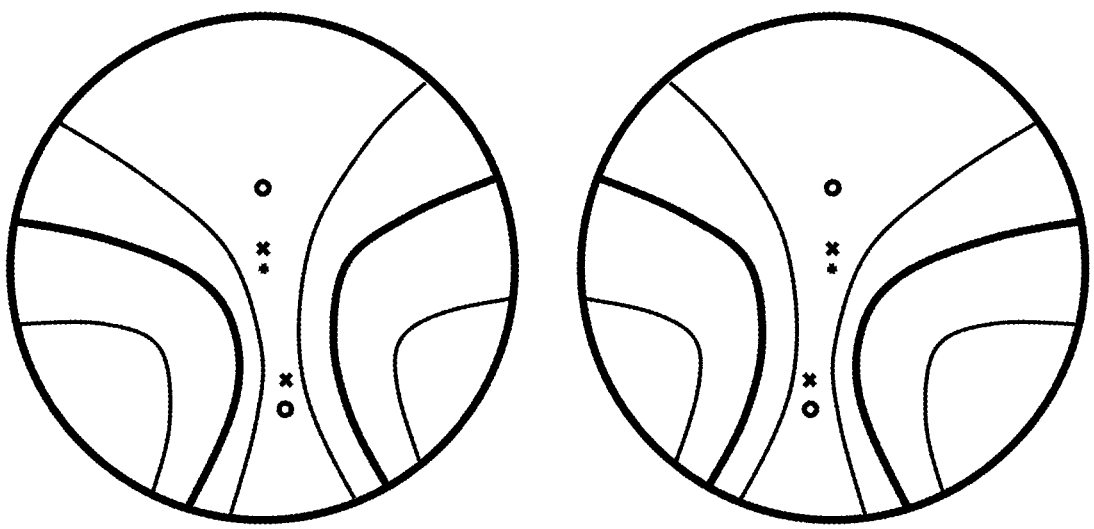
FIG. 20 (a) is an astigmatism view of the present invention designed suitably for the right eye of a user E, whereas (b) is an astigmatism view of the present invention designed suitably for the left eye of the user E.

When an order for lenses is placed with an eyeglass lens manufacturer from an optician's store, an obtained visual perception characteristic (defocusing characteristic) is imparted to the eyeglass lens manufacturer through a telephone or the Internet. Thereafter, a comparison is made between it and an average value, which has been beforehand calculated, of defocusing characteristics of many persons by use of a host computer of the eyeglass lens manufacturer, and a scale about how the visual perception of the user is characterized in comparison with standard visual perception is created. For example, if the pre-calculated average of the defocusing characteristics of many persons is 0.2 and if the defocusing characteristic of the user E is 0.4, it is understood that the reduction of visual perception does not easily occur in the user E even when a defocused state is reached. Therefore, in contrast to conventional lens design shown in FIG. 19, a lens having less distortion is designed and manufactured as decentralized design as in FIG. 20. Generally, the decentralized design has some apprehension about defocusing in a lateral part of a lens although the decentralized design has an advantage in less distortion, and, on the other hand, the user E has visual perception characterized in that defocusing is a lesser fear than other many users, and therefore the decentralized design shown in FIG. 20 is preferable to the design shown in FIG. 19.

Embodiment 13

Embodiment 13 is an example for measuring a visual perception characteristic of a user with respect to colors. Although this embodiment is an example in which measurement was performed in a laboratory by use of a magnetoencephalograph, it becomes possible to measure the characteristic of visual perception of a user with respect to colors and to provide a color lens or the like that reflects its measurement result in colors by using a similar visual stimulus object by use of an electroencephalograph in, for example, an optician's store.

1. Experimental Conditions and Brain Activity Recording

A grey fixation point is presented at the front at a visual distance of 100 cm, and the lattice figures of (a) and (b) of FIG. 1 are alternately displayed with a 66.67-millisecond period. At this time, the color of the lattice is set to be any one of white, red, blue, green, and yellow, and a subject is allowed to wear a colorless lens that has undergone eyesight correction, and the brain activity when the colors of the lattice that is a visual stimulus object are repeatedly displayed in random order for ten seconds in each color is measured by a magnetoencephalograph. Preferably, at this time, it is displayed two times or more in order to exclude the influence of ordering.

2. Analysis

Concerning the time when each lattice of white, red, blue, green, and yellow is displayed, an analysis window of 8 seconds is set among 10 seconds spent for measurement, and Fast Fourier Transform is performed, and the power value is calculated, and the root-sum-square (RSS) of the power value of a gradiometer pair in which the strongest reaction in the visual cortex has been measured is calculated. Thereafter, with respect to each color, the average value of the power value of the gradiometer pair is calculated.

3. Result

Figure 21:
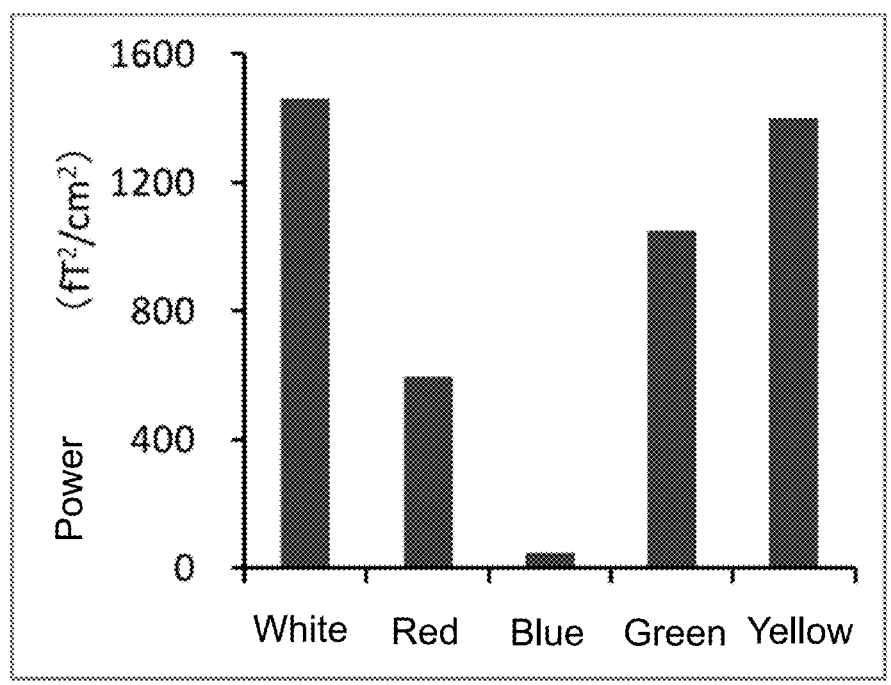
FIG. 21 A view showing a change in the brain reaction in a subject G when the lattice color is changed.

With respect to a subject G, a measurement result is shown in FIG. 21, in which the brain reaction becomes smaller in order of white yellow>green>red>blue according to a change in color of the lattice. At this time, it is understood that the ratio (blue/white) between white and blue is 0.03 as a result of calculation. Here, in order to evaluate the characteristic of the visual perception of the subject E, the ratio (blue/white) between white and blue of the average value of thirty subjects is beforehand calculated, and is compared with the ratio (blue/white)=0.03 between white and blue of the subject E. As a result, let it be supposed that the ratio (blue/white) between white and blue is low in the subject E in comparison with the entire average. In this case, it is understood that there is a tendency for the brain reaction when the subject E views blue to become smaller than the average and that the subject E has visual perception characterized in that blue is hard to view. From these facts, it is understood that it is preferable for the subject G to wear a lens that does not so much reduce the transmittance of blue, i.e., transmittance of a short wavelength of 500 nm or less by a color lens or the like, and therefore it is possible to set the transmittance of a lens in each wavelength and to design a color lens.

Figure 22:
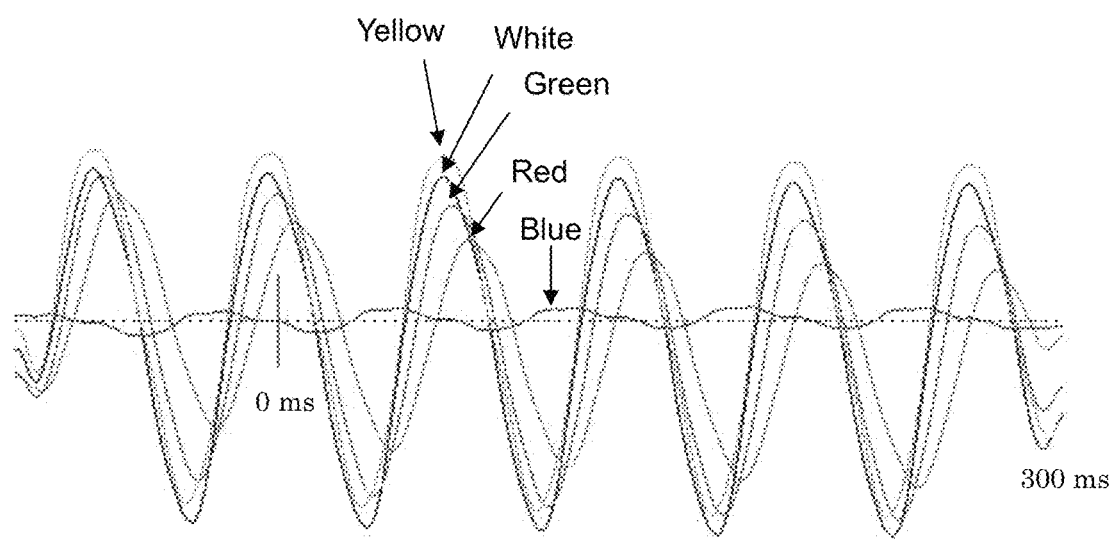
FIG. 22 A view of averaged waveforms by each lattice color in Embodiment 13.

Next, FIG. 22 shows averaged waveforms recorded by the gradiometer in which the strongest reaction in the visual cortex has been measured. When attention is paid to the phase, the order is white yellow>green>red>blue, and it is understood that the same result as the power value is obtainable even when the phase is used for evaluation. As thus described, it is possible to employ information on the power value and on the phase when visual perception concerning colors is evaluated.

It is also possible to modify and embody the present invention as follows.

Although two images that are visual stimulus objects inducing periodic brain waves are alternately displayed in the aforementioned embodiments as shown above, the number of kinds of images may be two or more. For example, if ten images that are equal to each other in the brightness of an entire image and in the amount of line segments (total line segment length) are prepared, and if these ten images are presented in random order, the interval of a presentation period of time of each image becomes the period of a periodic brain reaction induced by a visual stimulus object.

Although a display period of time and a non-display period of time of an image are set to be equal to each other in Embodiment 9, these are not necessarily required to be equal to each other. Although a stimulus-to-stimulus interval is 166.66 milliseconds as an example in Embodiment 9, a periodic brain reaction can be induced even if the display time is set as 100 milliseconds, and even if the non-display time is set as 66.66 milliseconds.

When a visual stimulus object that induces a periodic brain reaction is displayed, its periodicity may be changed. For example, a visual stimulus object is presented with a long period at the beginning, and its periodicity is gradually made fast, thus making it possible to objectively measure frequency that is recognizable to the subject.

The fixation point is not indispensable in being specifically displayed, and denotes that a subject is instructed to gaze at the direction of a sight line. For example, the fixation point of the present invention also includes the fact that the subject is instructed to view the center of a moving visual stimulus object and the fact that the subject is instructed to view a visual stimulus object having a visual angle of two degrees or less.

The length of the analysis window of the aforementioned embodiments is an example, and the present invention is not limited to this length.

Although an image is used as the presentation of a visual stimulus object in the aforementioned embodiments, the present invention includes the giving of a stimulus by using visual stimulus objects other than images, such as blinking with LED light or a color change.

The measurement method of user characteristics shown in Embodiment 11 is one example, and the present invention is not limited to this.

The defocusing characteristic shown in Embodiment 12 is one example, and the present invention is not limited to this.

The design example shown in Embodiment 12 is one example of aberration improvement, and the present invention is not limited to this.

The evaluation method of the characteristic of visual perception with respect to colors shown in Embodiment 13 is one example, and the present invention is not limited to this.

The color lens design method shown in Embodiment 13 is one example, and the present invention is not limited to this.

In a certain embodiment, a lens evaluation may be freely performed, for example, by the magnitude of a power value or by a gap between phases without being limited to a lens evaluation by the magnitude of amplitude.

Although right and left lens loads that differ from each other may be given as in Embodiment 4 or Embodiment 11 when the load of visual perception having a difference between a dominant eye and a non-dominant eye is given, the present invention also includes an arrangement in which a subject is allowed to wear, for example, polarizing lenses or liquid crystal lenses and in which right and left visual stimulus objects that differ from each other are presented to the subject without performing lens exchange by use of, for example, a stereoscopic display serving as a display on which the visual stimulus objects are displayed.

Although defocusing may be loaded by a lens worn by a subject when defocusing is loaded to the subject as in Embodiment 1 or Embodiment 12, the subject may be allowed to wear a lens having diopter power by which, for example, the subject visually well perceives the distance to a visual stimulus object, and a visual stimulus object that has been out of focus may be presented to the subject. In other words, the present invention also includes an arrangement in which, when the characteristic of visual perception of a subject brought about by defocusing is measured, the subject is allowed to wear a lens having diopter power by which the subject visually well perceives the distance to a visual stimulus object, and the subject is allowed to gaze at several kinds of visual stimulus objects in which the defocusing degree of the visual stimulus object has been changed.

Besides, the present invention is free to be performed in a mode that does not depart from the gist of the present invention.

The invention claimed is:

1. A method for creating eyeglass lenses, the method comprising:
   allowing a subject to wear a first lens to be evaluated;
   inducing a periodic brain activity by allowing the subject to view, through the first lens, a changing visual stimulus object that induces the periodic brain activity through the first lens;
   obtaining, via a device, the periodic brain activity as a waveform of an electrical signal during a total measurement time;
   calculating one or more of an amplitude, a power value, or a phase in a frequency that is an inverse number of a period of the periodic brain activity based on the waveform;
   evaluating an average visual perception or a time-dependent change in visual perception through the first lens based on the calculated one or more of the amplitude, the power value, or the phase in the frequency during an analysis window having a duration less than the total measurement time; and
   preparing a custom lens for the subject based on the evaluated average visual perception or time-dependent change in visual perception.

2. The method for according to claim 1, wherein a fixation point at which the subject is allowed to gaze is presented to the subject when the subject is allowed to view the visual stimulus object through the first lens.

3. The method according to claim 2, wherein the fixation point is displayed so as to be movable, and the subject is allowed to view the fixation point while the subject is moving a sight line.

4. The method according to claim 1, wherein the visual stimulus object is set to be movable.

5. The method according to claim 1, wherein the visual stimulus object is viewed by both eyes of the subject.

6. The method according to claim 5, wherein the one or more of the amplitude, the power value, or the phase that have been obtained as a result of viewing the visual stimulus object by both eyes of the subject are evaluated by comparison with one or more of a respective amplitude, power value, or phase that have been obtained as a result of viewing the visual stimulus object by one eye of the subject.

7. The method according to claim 5, wherein the one or more of the amplitude, the power value, or the phase that have been obtained as a result of viewing the visual stimulus object by both eyes of the subject are evaluated by comparison with one or more of a respective amplitude, power value, or phase that have been obtained as a result of viewing the visual stimulus object by left and right eyes of the subject through second and third lenses having mutually different conditions.

8. The method according to claim 5, wherein a balance of visual perception between both eyes of the subject is evaluated by the one or more of the amplitude, power value, or phase that have been obtained as a result of viewing the visual stimulus object by both eyes of the subject.

9. The method according to claim 1, wherein the visual stimulus object is viewed by a dominant eye of the subject, and the one or more of the amplitude, power value, or phase that have been obtained as a result of viewing the visual stimulus object by the dominant eye of the subject are evaluated by comparison with one or more of a respective amplitude, power value, or phase that have been obtained as a result of viewing the visual stimulus object by a non-dominant eye of the subject.

10. The method according to claim 1, wherein the average visual perception is evaluated, and the custom lens is prepared based on the evaluated average visual perception.

11. The method according to claim 1, wherein a plurality of lenses including the first lens are evaluated, each lens of the plurality of lenses having different lens characteristics relative to a remainder of the plurality of lenses.

12. The method according to claim 1, wherein the visual stimulus object comprises one line segment or a plurality of line segments, and evaluating the average visual perception includes evaluating a visual perception that changes depending on an axial direction of astigmatism.

13. The method according to claim 1, wherein the visual stimulus object comprises one circle or a plurality of circles, and a size of an astigmatic component is evaluated without evaluating a visual perception that changes depending on an axial direction of astigmatism.

14. The method according to claim 12, wherein the visual perception that changes depending on the axial direction of astigmatism is evaluated by alternately showing a first figure and a second figure that are components of the visual stimulus object, the first figure comprising one line segment or a plurality of line segments by which directionality with respect to a first direction is perceivable by the subject, the second figure comprising one line segment or a plurality of line segments by which directionality with respect to the first direction is perceivable by the subject and by which directionality in a second direction differing from the directionality of the first figure is perceivable by the subject.

15. The method according to claim 13, wherein the size of the astigmatic component is evaluated without evaluating visual perception that changes depending on the axial direction of astigmatism by alternately showing a first figure and a second figure that are components of the visual stimulus object, the first figure comprising one circle or a first plurality of circles by which directionality is unperceivable by the subject, the second figure comprising one circle or a second plurality of circles by which directionality different in arrangement from the directionality of the first figure is unperceivable by the subject.

16. The method according to claim 1, wherein the visual stimulus object is presented at a secondary position of an eye of the subject or at a tertiary position of the eye of the subject.

17. The method according to claim 1, wherein the visual stimulus object is continuously displayed without providing a period of time during which the visual stimulus object is not displayed.

18. The method according to claim 1, wherein the visual stimulus object is discontinuously displayed by providing a period of time during which the visual stimulus object is not displayed.

19. The method according to claim 1, wherein the visual stimulus object comprises a plurality of and two or more kinds of visual stimulus objects, and the plurality of visual stimulus objects are equal in brightness to each other.

20. The method according to claim 1, wherein the frequency that is the inverse number of the period of the periodic brain activity is 4 to 60 Hz.

21. The method according to claim 1, wherein the periodic brain activity is a visual evoked magnetic field in a steady state.

22. The method according to claim 1, wherein the periodic brain activity is a visual evoked potential in a steady state.

23. The method according to claim 1, wherein the method includes evaluating an average visual perception for a plurality of lenses including the first lens and a second lens different from the first lens, wherein the first lens is a progressive power lens, and wherein preparing the custom lens comprises:
   a first step of obtaining a difference in an optical performance value between the progressive power lens and the second lens, the optical performance value being based on the one or more of the amplitude, power value, or phase in frequency;
   a second step of calculating a lens shape with a corrected optical performance value as a target value so as to set a reference lens to be evaluated, the corrected optical performance value being based on the obtained difference in optical performance value between the progressive power lens and the second lens;
   a third step of obtaining a difference in an optical performance value between the reference lens and the progressive power lens; and
   a fourth step of calculating a new lens shape with a new corrected optical performance value based on the obtained difference in optical performance value between the reference lens and the progressive power lens, the new corrected optical performance value being a new target value so as to reset the reference lens to be evaluated; and
   wherein the third step and the fourth step are repeated at least once to reduce the difference between the obtained difference in optical performance value between the reference lens and the progressive power lens, the reference lens being the custom lens.

24. The method according to claim 1, wherein the time dependent change in visual perception is evaluated by calculating the one or more of an amplitude, power value, or phase during two or more analysis windows each having a duration less than the total measurement time, and the custom lens is prepared based on the time dependent change in visual perception.

25. The method according to claim 23, wherein the third step includes obtaining a difference in an optical performance value among the reference lens, the progressive power lens, and at least one additional lens, and the new corrected optical performance value of the fourth step is based on the obtained difference among the reference lens, the progressive power lens, and the at least one additional lens.

* * * * *